(12) United States Patent
Hay, Jr. et al.

(10) Patent No.: US 6,718,832 B1
(45) Date of Patent: Apr. 13, 2004

(54) METHOD AND APPARATUS FOR MEASURING PHYSICAL PROPERTIES OF MATTER

(76) Inventors: John C. Hay, Jr., 709 Battlefront Trail, Knoxville, TN (US) 37922; Barry N. Lucas, 520 Westwood Dr., Maryville, TN (US) 37803

( * ) Notice: Subject to any disclaimer, the term of this patent is extended or adjusted under 35 U.S.C. 154(b) by 0 days.

(21) Appl. No.: 10/306,575

(22) Filed: Nov. 27, 2002

Related U.S. Application Data

(63) Continuation-in-part of application No. 10/212,618, filed on Aug. 5, 2002, now Pat. No. 6,637,265, which is a continuation-in-part of application No. 09/664,023, filed on Sep. 19, 2000, now abandoned.

(51) Int. Cl.$^7$ .............................................. G01N 9/36
(52) U.S. Cl. .................................. 73/790; 73/819; 73/37
(58) Field of Search .......................... 73/37, 433, 437, 73/149, 790, 818, 819, 1.57

(56) References Cited

U.S. PATENT DOCUMENTS

| | | |
|---|---|---|
| 3,747,416 A | 7/1973 | Wommack |
| 4,083,228 A | 4/1978 | Turner et al. |
| 4,112,738 A | 9/1978 | Turner |
| 4,369,652 A | 1/1983 | Gundlach |
| 4,708,016 A | 11/1987 | Akegi |
| 4,770,041 A | 9/1988 | Bearce |
| 5,052,405 A | 10/1991 | Batchelder |
| 5,074,146 A | 12/1991 | Orr et al. |
| 5,595,189 A | 1/1997 | Naim et al. |
| 5,606,126 A | 2/1997 | Glenville |
| 6,578,431 B2 * | 6/2003 | Dillard et al. ................. 73/819 |

OTHER PUBLICATIONS

Horace A. Bowman, Randall M. Schoonover, "Procedure for High Precision Density Determinations by Hydrostatic Weighing", Journal of Research of the NBS–C Engineering and Instrumentation, vol. 71C, No. 3, Jul.–Aug. 1967, pp. 179–198.

* cited by examiner

Primary Examiner—John E. Chapman
(74) Attorney, Agent, or Firm—Luedeka, Neely & Graham, P.C.

(57) ABSTRACT

The invention provides a method and apparatus for determining a relationship between hydrostatic stress and volumetric strain in a sample of compressible material, where the sample is immersed in a fluid medium having a density. The method includes steps of varying the hydrostatic stress on the sample by changing the density of the fluid medium over a range of densities, determining a change in apparent weight of the sample as the density of the fluid medium is changed, and determining the volumetric strain in the sample based on the change in apparent weight of the sample and the change in density of the fluid medium.

23 Claims, 19 Drawing Sheets

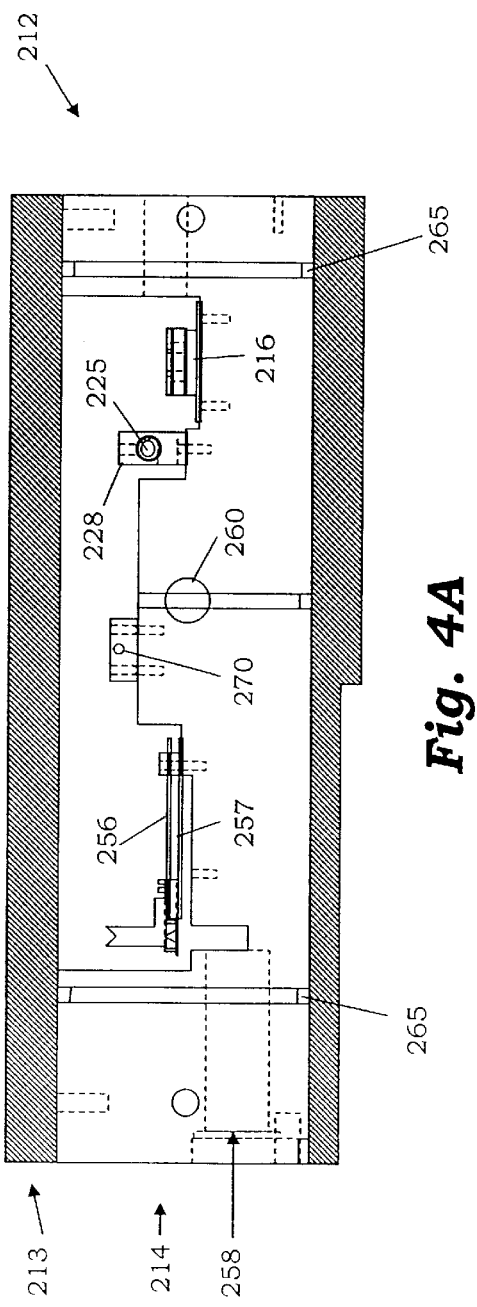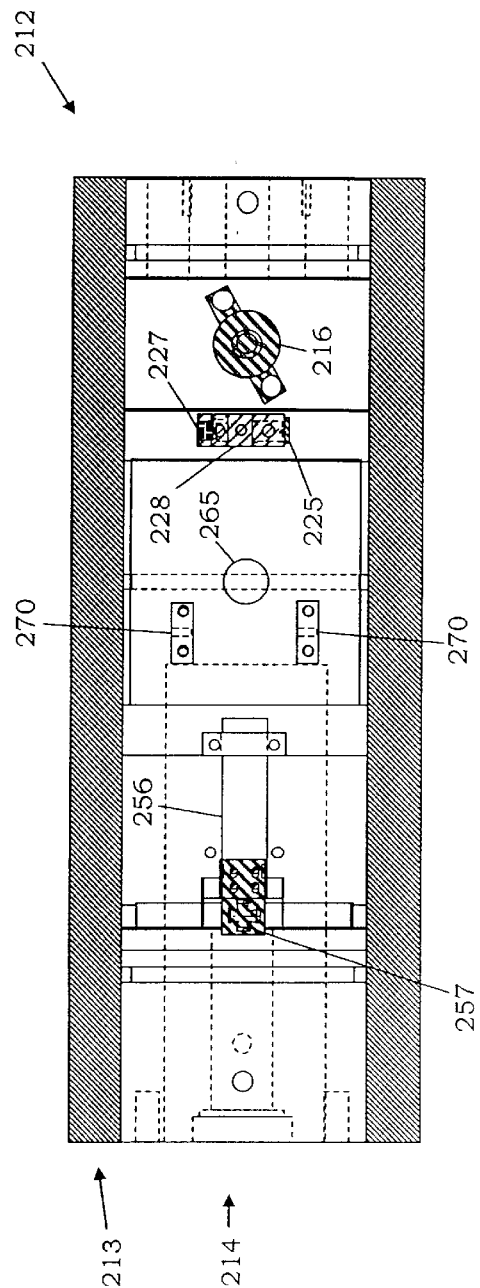

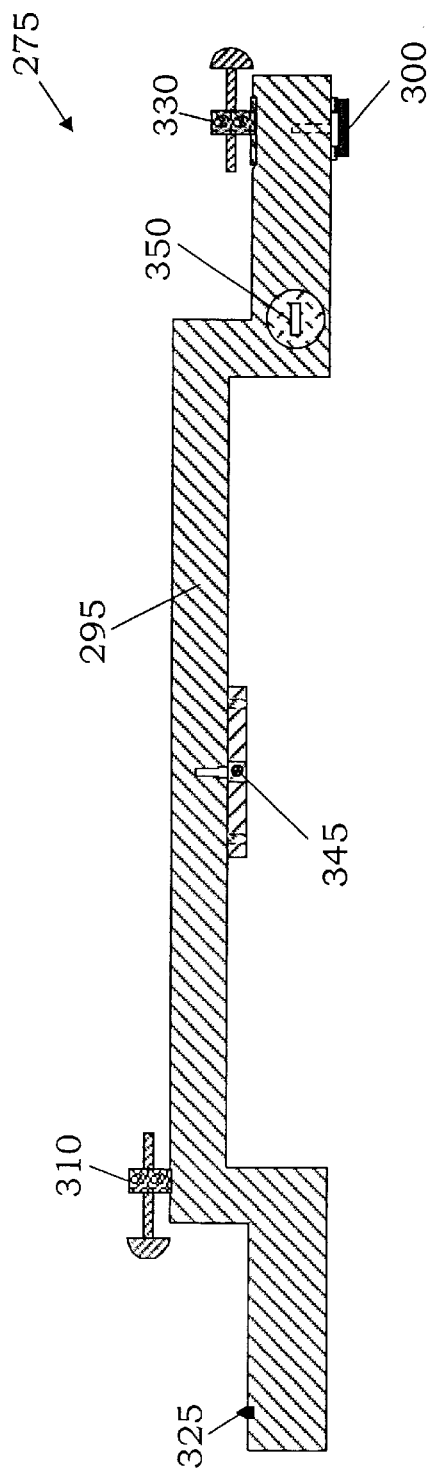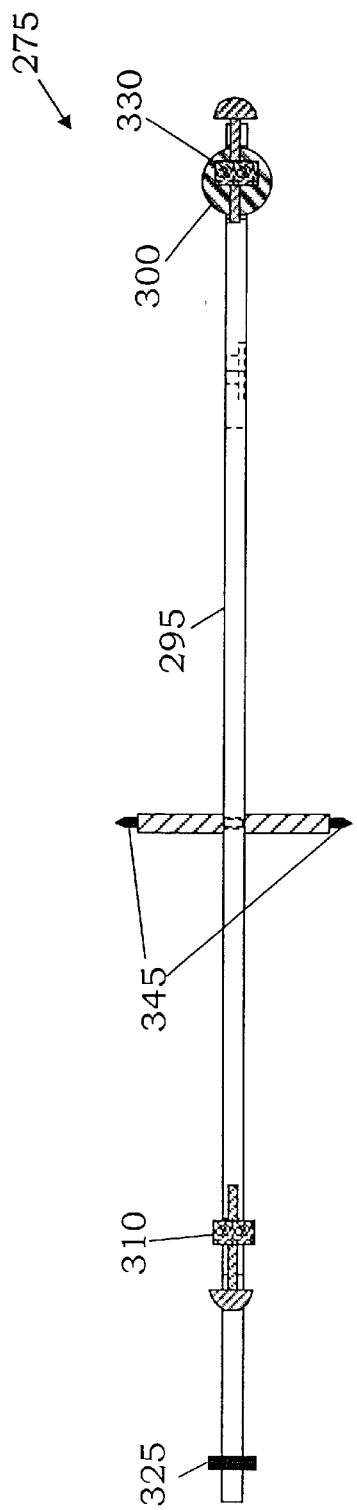
Fig. 5A
Fig. 5B

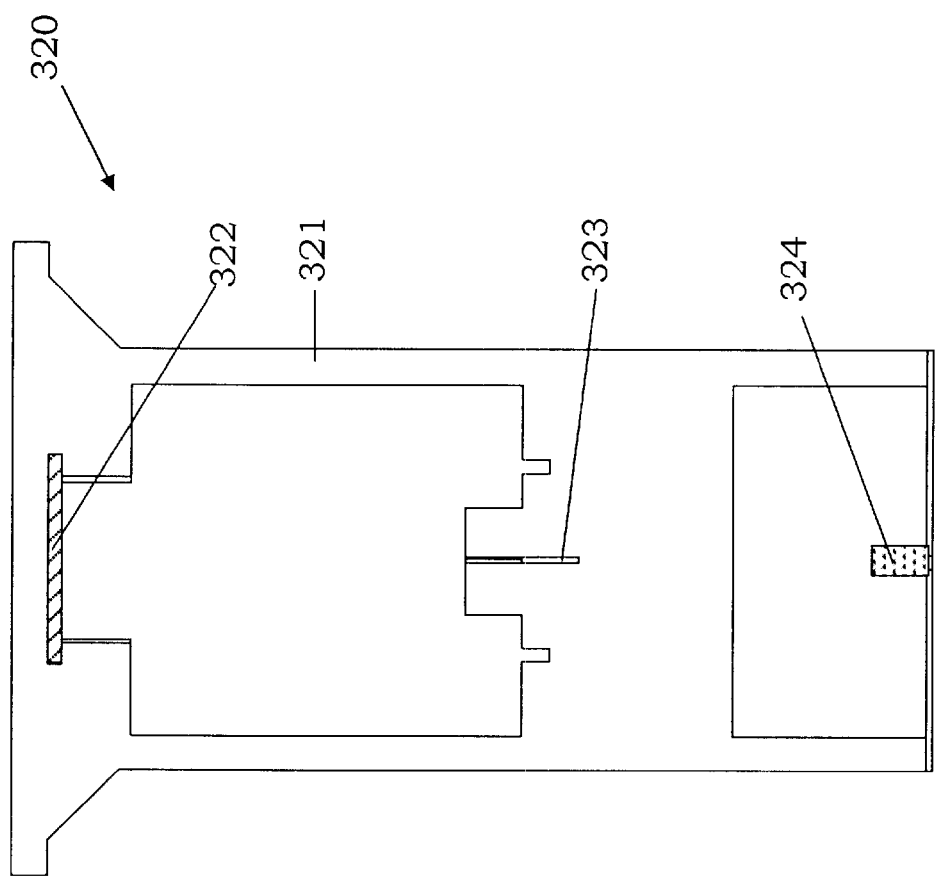
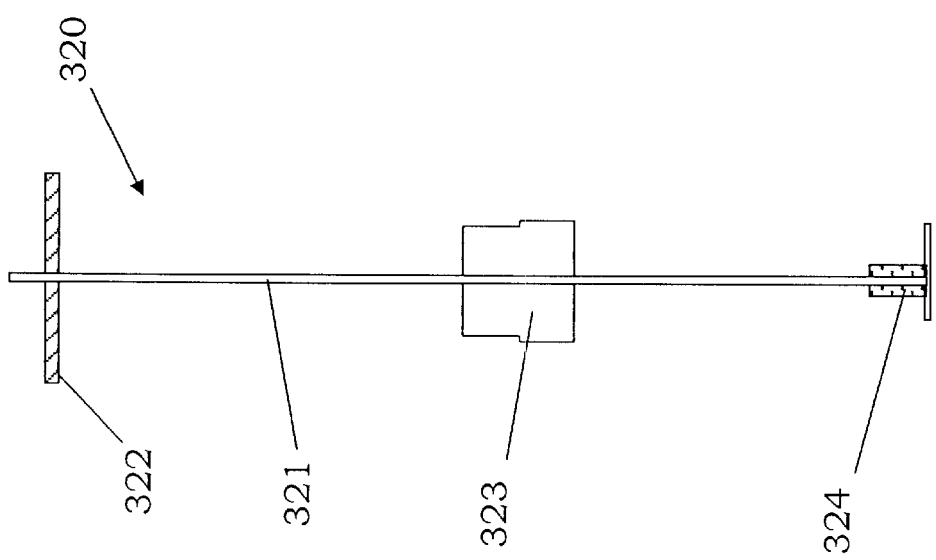
Fig. 7B
Fig. 7A

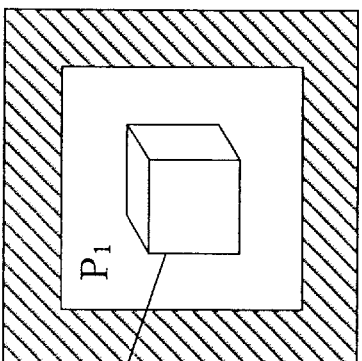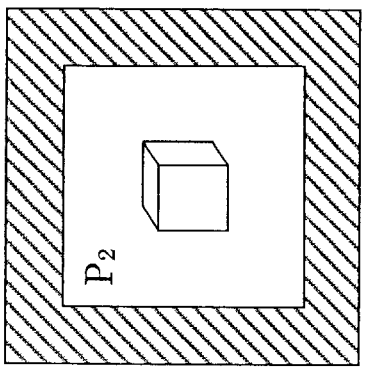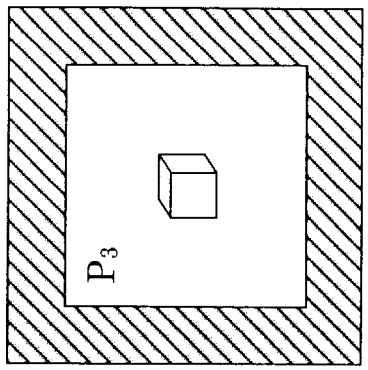
$P_3 > P_2 > P_1$
Fig. 13

METHOD AND APPARATUS FOR MEASURING PHYSICAL PROPERTIES OF MATTER

This application is a continuation-in-part of co-pending application Ser. No. 10/212,618 filed Aug. 5, 2002, now U.S. Pat. No. 6,637,265, entitled Method and Apparatus for Measuring Physical Properties of Matter which is a continuation-in-part of patent application Ser. No. 09/664,023 filed Sep. 19, 2000, entitled Method and Apparatus for Measuring Physical Properties of Matter, now abandoned.

TECHNICAL FIELD

The present invention relates to a method and apparatus for measuring physical properties of a sample of matter, including the mass, volume, density, and bulk modulus. More particularly, the invention relates to a method and apparatus which automatically measures a stress/strain relationship of compressible material.

BACKGROUND OF THE INVENTION

Several physical properties of matter can be determined from measurements of sample mass, volume, and changes in volume with respect to the specific environment in which the measurements are conducted. For instance, the density of matter may be determined from the mass and volume, as will be briefly described below. Under other testing conditions it is also possible to measure the bulk modulus, or compressibility, of a material by employing some of the same measurement methods.

The density of a substance is expressed as a ratio of mass m to volume V, or m/V. This is a physical property of a material which relates to composition, level of impurities, and mixtures, and can be an indicator of hidden features such as voids. In the case of compressible media, such as closed-pore solids, the bulk density is a function of hydrostatic pressure, since the volume changes but the mass remains constant.

There exist two popular methods for determining the density of a solid: (1) by comparison of the sample density with the densities of substances of known value, usually by hydrostatic weighing in two different fluids of known and substantially different density (Archimedes principle), and (2) by the independent measurement of mass and volume of the sample.

Considering the first method, the weight of an object is measured in two liquids having significantly different densities. The measured weight, also referred to herein as apparent weight, is reduced from the true weight due to buoyancy forces acting on the object. Thus, the apparent weight is the true weight minus the buoyancy force, where the buoyancy force is equal to the weight of the liquid displaced by the object. When in the higher density liquid, the buoyancy force acting on the object is greater, and the apparent weight of the object is less. The sensitivity of the method ultimately relies on the range in available liquid densities. In one method of using hydrostatic weighing techniques, one measures the apparent weight of an object in alcohol and then in water, where the alcohol and the water have densities of 0.791 and 1.0 g/cc, respectively. It is also common practice to weigh the object in air and then in water or alcohol, thus using air as the first medium. In that case it is common practice to assume the weight in air to be the "true weight" of the object. The specific reasons for using a liquid as one of the mediums in this technique are (i) to obtain a large difference in density between the two fluids, and (ii) to increase the effect of buoyancy forces.

For very accurate measurement of density, there are several experimental problems which are typically ascribed to the hydrostatic weighing method using two liquids. First, the method suffers from the necessity of weighing an object in liquid. Strictly as a practical matter, this requires suspending the object via a tether or thin wire in the liquids. Second, related to the first, is the fact that surface tension forces affect the measurement as the liquid meniscus either pulls the tether down into the liquid or pushes it up into the adjacent gas (typically air), depending on whether the liquid wets the tether easily. Third, the density of the liquid is affected by dissolved gases in the liquid. Since the effect of trapped gas is to change the actual density of the liquid, efforts must be made to eliminate the trapped gas. Fourth, results will vary due to bubbles of trapped gas on irregular sample surfaces of the object. The bubbles that cling due to surface tension displace liquid and affect the measured buoyancy forces.

The second common approach to determine density requires independent determination of both the mass and the volume. One measures the mass of the body using conventional state-of-the-art balances common to most laboratories. Commercial devices exist for performing this step to very high precision and accuracy. The volume is determined independently. If the sample is of a uniform geometry, it may be possible to calculate the specimen volume based on measurable dimensions. In the more general case where samples are of irregular shape, the volume is determined by a method commonly referred to as pycnometry. For reasonably sized samples on the order of 0.5 cubic centimeters and larger, commercial pycnometers are available for determining volume to 0.02%. Pycnometers typically consist of two chambers connected by means of a pathway for a gas to move and a valve which can isolate the two chambers. The exact volume of one of the chambers must be known apriori. The second chamber is of arbitrary, but similar size. The first chamber, of known volume, is pressurized using a gas such as helium to a predetermined pressure. The second chamber is initially empty and is evacuated by means of a vacuum pump. By means of valves, the two chambers are then isolated from the gas source and from the vacuum pump leaving the first chamber at an elevated pressure with helium and the second chamber under vacuum. The valve in the passageway connecting the two chambers is then opened and the pressurized gas is allowed to expand from the first chamber into the second chamber, and the pressure achieves a new equilibrium value by virtue of the increased volume occupied by the gas. It is a straightforward calculation to determine the volume of the unknown chamber using the initial helium pressure in the first chamber, the volume of the first chamber, and the final pressure. The steps are then repeated with the sample of interest being placed into the second chamber. The newly calculated volume of the second chamber represents the remaining volume of the second chamber not occupied by the sample.

Although the field of pycnometry is well established for accurately determining the volumes of solids of reasonable sizes, the state-of-the-art is limited by several factors in attempts to extrapolate to smaller samples. There are many industries where large samples are not always available. Some specific applications would include high-temperature superconducting wires, samples pertaining to the study of irradiation, and porous membranes used for delivering and mixing gases, such as in the fuel cell applications. The volume of such samples is often much smaller than that required by pycnometers. For accurate measurements, the sample should occupy a significant fraction of the chamber volume, e.g. 50–60% of a 1 cubic centimeter chamber.

There are several other limitations to the pycnometry method for determining density. First, if safeguards are not included, temperature variations of the gas due to room temperature fluctuations may affect the pressure, and hence the density, of the pressurized gas. Second, the gas-comparison pycnometer described above does not work if there are any leaks in the system. The ability of the technique to work depends strongly upon the number of gas atoms remaining constant before and after the gas expands into the second chamber. Third, the chamber door, when closed, must close in a repeatable fashion such that the volume of the chamber is exactly the same every time the door is opened and closed. Fourth, the mechanism requires a vacuum pump. Fifth, the true volume of the pressurized chamber must be known to better tolerances than the desired accuracy of sample volume. Finally, the mass must be measured by a separate device.

Further, it is difficult, if not impossible, to determine the bulk modulus of a material by Archimedes method using the conventional procedure briefly described above for at least two reasons. First, the problems identified above with measuring the weight of samples in liquids apply as well in a bulk modulus measurement. Second, to measure bulk modulus, or compressibility, the method must affect a change in volume by a change in hydrostatic stress. As a practical matter, one cannot cause significant changes in stress or volume by simple submersion in a typical laboratory environment. For example, to generate a meager stress of 14 psi on a sample submerged in a column of water, the water column would have to be 34 feet tall.

Thus, there are significant limitations associated with the prior art with respect to density and bulk modulus measurements. The current invention offers significant improvements over the prior art, as will become apparent in the following description of invention.

SUMMARY OF THE INVENTION

The foregoing and other needs are met by a method for determining a relationship between hydrostatic stress and volumetric strain in a sample of compressible material, where the sample is immersed in a fluid medium having a density. The method includes the steps of varying the hydrostatic stress on the sample by changing the density of the fluid medium over a range of densities, determining a change in apparent weight of the sample as the density of the fluid medium is changed, and determining the volumetric strain in the sample based on the change in apparent weight of the sample and the change in density of the fluid medium.

An underlying assumption of prior methods for measuring density is that the sample is "incompressible". By definition, incompressible matter maintains a constant volume with applied stress. While applied stresses always yield some finite strain, most dense engineering materials are practically incompressible.

According to preferred embodiments of the invention, one may determine the bulk modulus, or compressibility, of compressible materials. The bulk modulus describes the volumetric strain when matter is exposed to a hydrostatic stress. The bulk modulus, K, is given by $$K = \frac{\sigma}{\Delta V / V_1} = \frac{1}{B},$$

where $\sigma$ is the hydrostatic stress, $V_1$ is the initial volume of the sample prior to an applied stress, and $\Delta V$ is the change in volume due to the applied hydrostatic stress. The compressibility, B, is the reciprocal of the bulk modulus.

In preferred embodiments of the invention, the method described above further comprises changing the density of the fluid medium from an nth density, $\rho_n$, to an nth+1 density, $\rho_{n+1}$, and determining an nth apparent weight of the sample $W_n$ at the nth density and an nth+1 apparent weight of the sample $W_{n+1}$ at the nth+1 density. The volumetric strain in the sample is determined according to:

$$\frac{\Delta V}{V_1} = \frac{W_n - W_{n+1}}{V_1 \times (\rho_n - \rho_{n+1})} - 1,$$

where $V_1$ is an initial volume of the sample at an initial density, and $\Delta V / V_1$ is the volumetric strain.

In another aspect, the invention provides a method for operating an apparatus to determine bulk modulus of a sample, where the apparatus includes a beam balance enclosed within a pressure chamber, and the beam balance includes a sample pan coupled to a first end and a counter-force application device disposed at an opposing second end. The apparatus also includes a calibration standard of known density, a temperature sensor, and a pressure sensor. The method includes the steps of sealing the sample within the pressure chamber, purging the pressure chamber of air, and pressurizing the chamber to an nth pressure using a fluid medium. With the sample on the sample pan and the pressure chamber pressurized to the nth pressure, an nth force is determined, where the nth force is applied by the counter-force application device as required to balance the beam balance. Using the temperature sensor and the pressure sensor, the nth temperature and the nth pressure within the pressure chamber are measured. Based upon a predetermined relationship between density, pressure, and temperature of the fluid medium, an nth density of the fluid medium is calculated.

The method further includes pressurizing the chamber to an nth+1 pressure, which is different from the nth pressure. With the sample on the sample pan and the pressure chamber pressurized to the nth+1 pressure, an nth+1 force required to balance the beam balance is determined, which is applied by the counter-force application device. Using the temperature sensor and the pressure sensor, the nth+1 temperature and the nth+1 pressure within the pressure chamber are measured. Based upon the predetermined relationship between density, pressure, and temperature of the fluid medium, an nth+1 density of the fluid medium is calculated. The bulk modulus of the sample is then calculated based at least in part on the nth and nth+1 densities of the fluid medium and the nth and nth+1 forces applied by the counter-force application device.

In yet another aspect, the invention provides an apparatus for determining bulk modulus of a sample that is immersed in a fluid medium having variable density while exposed to an acceleration in a first direction and a net buoyancy force in a second direction opposite the first direction, where the net buoyancy force is a sum of buoyancy forces in the first and second directions exerted on the sample by the fluid medium. The apparatus comprises a chamber for containing the fluid medium and the sample immersed in the fluid medium, and means for selectively varying the density of the fluid medium in the chamber over a range of densities. The apparatus also includes means for producing at least one electrical signal related to the density of the fluid medium in the chamber as the density of the fluid medium is varied.

A beam balance, having opposing first and second ends, is disposed within the chamber. The beam balance includes a sample pan disposed adjacent the first end of the beam balance. The sample pan has a sample pan volume and a sample pan mass, and creates a sample pan moment adjacent the first end of the beam balance. A first counter-weight is disposed adjacent the second end of the beam balance. The first counter-weight has a first counter-weight volume which is substantially equivalent to the sample pan volume, and a first counter-weight mass which is substantially equivalent to the sample pan mass. Thus, the first counter-weight creates a first counter-weight moment adjacent the second end of the beam balance that is substantially equivalent to the sample pan moment.

A coil assembly, which is disposed adjacent the second end of the beam balance, has a coil assembly volume and a coil assembly mass, and creates a coil assembly moment adjacent the second end of the beam balance. The coil assembly is electrically coupled to a controller. A magnet assembly is disposed adjacent to and magnetically interacts with the coil assembly.

A second counter-weight, which is disposed adjacent the first end of the beam balance, has a second counter-weight volume which is substantially equivalent to the coil assembly volume, and a second counter-weight mass which is substantially equivalent to the coil assembly mass. The second counter-weight creates a second counter-weight moment adjacent the first end of the beam balance that is substantially equivalent to the coil assembly moment.

The controller provides a coil current to the coil assembly, thereby generating a magnetic field that interacts with the magnet assembly. The interaction between the magnetic field of the coil assembly and the magnet assembly causes a force to be applied to the second end of the beam to keep the beam balanced as the density of the fluid medium in the chamber is varied over the range of densities. The force applied to the second end of the beam is substantially equivalent to the difference between the net buoyancy force and the product of the sample mass times the acceleration while the sample is immersed in the fluid medium as the density of the gaseous medium is varied over the range of densities.

A computing device receives the at least one electrical signal related to the density of the fluid medium and at least one electrical signal related to the coil current, and based thereon calculates the bulk modulus of the sample.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements throughout the several drawings as follows:

FIGS. 4A–4B depict two views of a gas chamber according to a preferred embodiment of the invention;

FIGS. 5A–5B depict two views of a beam balance according to a preferred embodiment of the invention;

FIGS. 7A–7B depict two views of a sample holder according to a preferred embodiment of the invention;

FIG. 13 depicts a cube exposed to various levels of hydrostatic pressure;

DETAILED DESCRIPTION OF THE INVENTION

Figure 1:
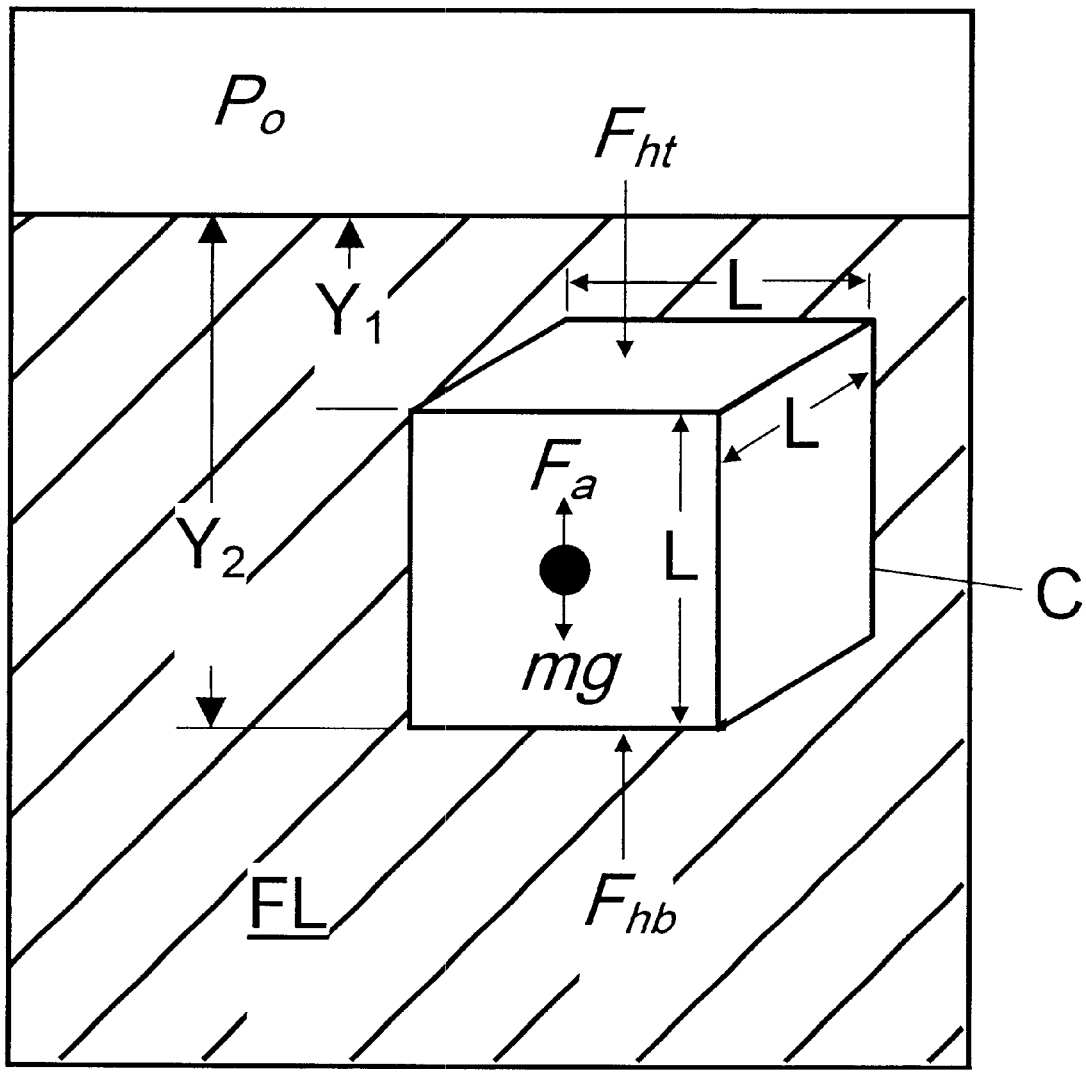
FIG. 1 depicts a cubic sample affected by hydrostatic forces while submerged within a fluid medium.

To aid in understanding the -operation of the invention, the general concept of hydrostatic weighing is first described. Shown in FIG. 1 is a solid incompressible cube C, having a volume V and sides of length L, submerged in a fluid medium FL. As one skilled in the art will appreciate, the terms "fluid medium" and "fluid", as used in the discussion of FIG. 1, as used in the description of preferred embodiments of the invention, and as used in the claims that follow, may refer to any substance which cannot sustain a shear stress. Thus, a fluid or fluid medium may be a gas, a mixture of gases, a liquid, a mixture of liquids, or a mixture of gases and liquids. Similarly, the phrase "gaseous medium" as used herein refers to a gas or a mixture of gases.

Forces acting on the cube C include (1) the actual weight of the cube, mg, due to the cube's mass m and the local gravitational acceleration g, (2) hydrostatic forces $F_{ht}$ and $F_{hb}$ caused by hydrostatic pressure on the top and bottom surfaces of the cube, and (3) an applied force $F_a$ to maintain the cube in static equilibrium. The applied force $F_a$ is equivalent to the apparent weight of the cube when submerged in the fluid. The hydrostatic pressure on the top surface of the cube is expressed as $P_0+\rho g Y_1$, and on the bottom surface as $P_0+\rho g(Y_1+L)$, where $\rho$ is the density of the displaced fluid, $Y_1$ is the distance from the top surface of the cube to the surface of the fluid, and $P_0$ is the pressure on the surface of the fluid. The resulting hydrostatic forces $F_{ht}$ and $F_{hb}$ on the top and bottom surfaces of the cube are expressed as $(P_0+\rho g Y_1)L^2$ and $(P_0+\rho g(Y_1+L))L^2$, respectively. The sum of the hydrostatic forces is a buoyancy force acting on the cube, which is equivalent to the weight of the fluid displaced by the cube. For static equilibrium, the sum of the forces is zero, as expressed by:

$$F_a - mg - F_{ht} + F_{hb} = 0, \tag{1}$$

$$F_a - mg - (P_0+\rho g Y)L^2 + (P_0+\rho g(Y+L))L^2 = 0, \tag{2}$$

$$F_a - mg + \rho L^3 g = 0, \tag{3}$$

$$F_a - mg + \rho V g = 0, \tag{4}$$

$$F_a = mg - \rho V g. \tag{5}$$

According to equation (5), the apparent weight of the cube, $F_a$, is the true weight, mg, minus the buoyancy force, $\rho Vg$. Thus, as the fluid density $\rho$ increases, the buoyancy force acting on the cube increases, and the apparent weight of the sample decreases.

Applying the Archimedes principle, if a sample is submersed in a fluid wherein the fluid density may be adjusted to two different densities, equation (5) can be solved simultaneously to yield the sample's density according to:

$$\rho_o = -\frac{F_{a1}\rho_2 - F_{a2}\rho_1}{F_{a2} - F_{a1}} \quad (6)$$

where $\rho_0$ is the density of the sample, $\rho_1$ and $\rho_2$ are the two different fluid densities, and $F_{a1}$ and $F_{a2}$ are the apparent weights of the sample in the two different fluid densities.

A key innovative element of this invention that offers significant improvement over prior art is the recognition that the sensitivity of Archimedes' method relies on achieving as large a change in fluid density as possible. Another key innovation of the present invention is that the fluid is preferably a gas for both weight measurements, a significant improvement on the usual method of implementing Archimedes' method.

To achieve the greatest accuracy in measuring sample density when the two measurement fluids are both gasses, one must change the density of the gas as much as possible. In essence, for a given weighing device the accuracy of the measured sample density depends on the range of employed fluid densities. Thus, if one does not desire great accuracy, a small change in fluid density may suffice, but the greatest accuracy in the sample density measurement is achieved by changing the fluid density as much as possible.

For illustrative purposes, an error analysis will provide a foundation for understanding that the desired accuracy is tied to the available range of fluid density of the gaseous medium. An assumption that will be made at this point is that the balance used for weighing the sample is of an appropriate size for the sample. That is, large errors will result if one were to use a 1000 kg load cell to measure a sample weighing 1 mg. Thus, this analysis assumes that the sample weight utilizes at least $\frac{1}{10}^{th}$ of the full range of the weighing device.

The total uncertainty of the measured quantity can be determined from a standard engineering analysis. The total uncertainty, as a percentage, is given by:

$$U = [(\partial \rho_o/\partial F_{a1} U_{Fa1})^2 + (\partial \rho_o/\partial F_{a2} U_{Fa2})^2 + (\partial \rho_o/\partial \rho_1 U_{\rho 1})^2 + (\partial \rho_o/\partial \rho_2 U_{\rho 2})^2]^{1/2}/\rho_o \quad (7)$$

where $U_{Fa1}$, $U_{Fa2}$, $U_{\rho 1}$ and $U_{\rho 2}$ are the absolute uncertainties in $F_{a1}$, $F_{a2}$, $\rho_1$, and $\rho_2$, respectively, and $\partial \rho_o/\partial F_{a1}$, $\partial \rho_o/\partial F_{a2}$, $\partial \rho_o/\partial \rho_1$, and $\partial \rho_o/\partial \rho_2$ are the partial derivatives of equation (6) with respect to the four measured quantities on the right-hand-side of equation (6). They are determined as follows:

$$\partial \rho_o/\partial F_{a1} = F_{a2}(\rho_1 - \rho_2)/(F_{a1} - F_{a2})^2, \quad (8)$$

$$\partial \rho_o/\partial F_{a2} = F_{a1}(\rho_2 - \rho_1)/(F_{a1} - F_{a2})^2, \quad (9)$$

$$\partial \rho_o/\partial \rho_1 = -F_{a2}/(F_{a1} - F_{a2}), \text{ and} \quad (10)$$

$$\partial \rho_o/\partial \rho_2 = F_{a1}/(F_{a1} - F_{a2}). \quad (11)$$

In The following examples illustrate the importance of the fluid density range in achieving a high accuracy in the measured sample density. In the cases below, it is assumed that there is no uncertainty in the gas density measurement. This will limit the discussion to the best case measurements given state of the art balances.

Case 1: Aluminum
  Density: 2.699 g/cc
  Volume: 0.003 cc
  $\rho_1$: 0.005 g/cc
  $\rho_2$: 0.120 g/cc
  From, equation (5) then,
  $F_{a1}$: 7.94e-5 N
  $F_{a2}$: 7.60e-5 N
  Balance uncertainty: 13.12 nN (23 ppm)
  $UF_{a1} = UF_{a2} = 1.3\text{e-}8\text{N}$
  $U\rho_1 = U\rho_2 = 0$ The total uncertainty for the sample density is 0.54%. That is, one could expect the measured sample density to be between 2.684 and 2.713 g/cc.

Case 2: Aluminum
  Density: 2.699 g/cc
  Volume: 30 cc
  $\rho_1$: 0.005 g/cc
  $\rho_2$: 0.120 g/cc
  From equation (5) then,
  $F_{a1}$: 0.794 N
  $F_{a2}$: 0.760 N
  Balance uncertainty: 131.2 nN (23 ppm)
  $UF_{a1} = UF_{a2} = 1.3\text{e}4\text{N}$
  $U\rho_1 = U\rho_2 = 0$ In this case it is assumed that the accuracy of the balance, as a function of full scale, has remained the same. It is assumed that a balance with a greater range has been used. The important point here is that the accuracy has not changed. Using these values in the uncertainty analysis again results in a 0.54% uncertainty. Thus, as long as one compares balances of equal accuracies over their full scale, the accuracy will not depend on the size or volume of the sample.

Figure 2:
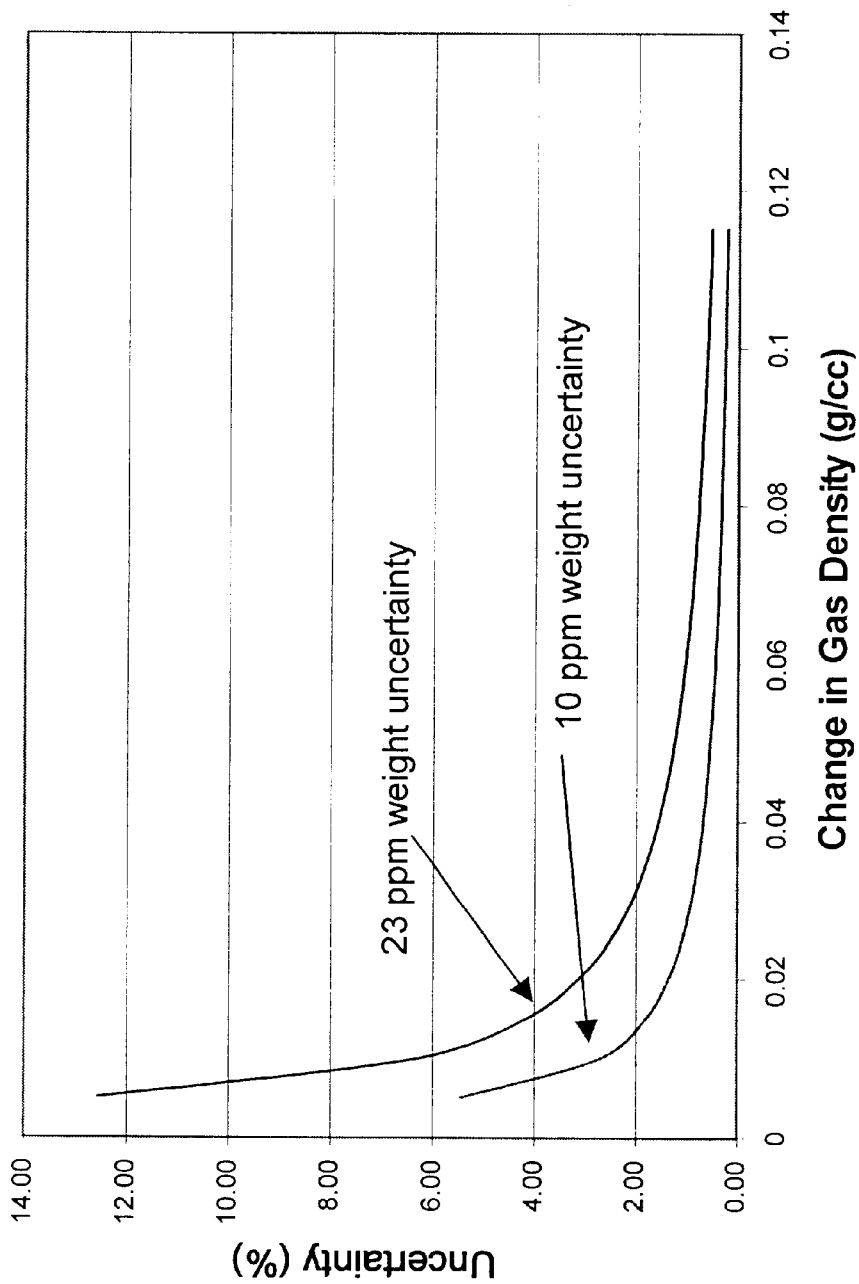
FIG. 2 graphically depicts a relationship of measurement uncertainty versus change in gas density.

On the other hand, the accuracy depends very strongly on the difference between the two gas densities used. For instance, if $\rho 2$ is varied (and hence $F_{a2}$) over a wide range of values, the overall uncertainty in the measurement will also vary. This function is summarized in FIG. 2. For clarity, the uncertainty in the measured density does depend on the overall uncertainty of the load measurement. These calculations have been performed assuming that the only source of uncertainty is in the weight measurement.

The uncertainty analysis indicates that if one tailors the dynamic range, or maximum capacity, of the system to the sample of interest the uncertainty in the sample density is a function of the gas density change only. This assumes that the relative accuracy of the balance is constant, but this is reasonable since balances, both large and small, can typically achieve 10 ppm accuracies.

Therefore, it is most preferable to select a gas system that can achieve the greatest change in density as possible. As discussed above, the desired characteristics of the gas selected include a rapid change in density with change in pressure, a known equation of state, and that it can be densified without liquefying first.

Figure 3:
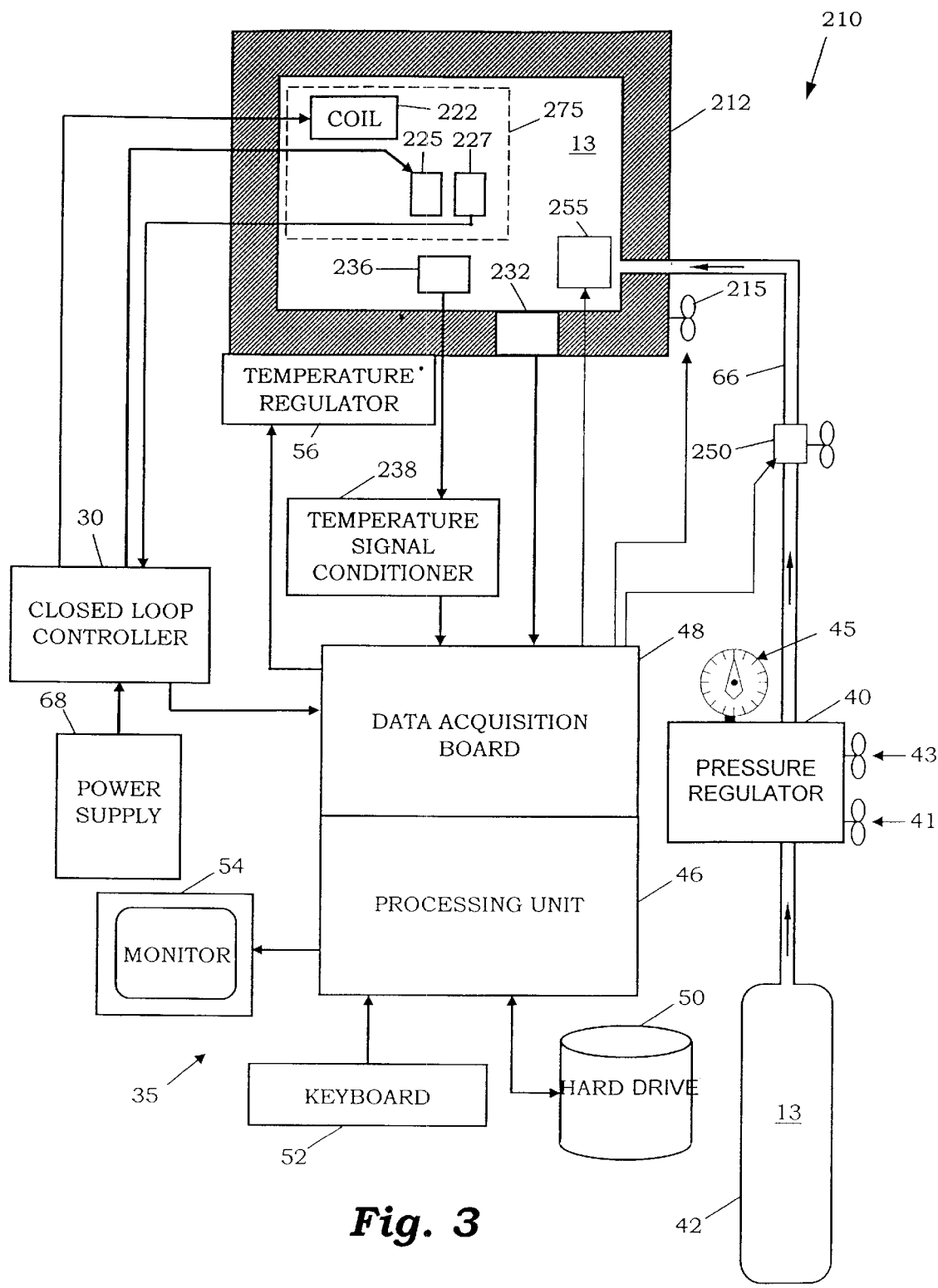
FIG. 3 depicts a density and bulk modulus measurement system according to a preferred embodiment of the invention.

In the preferred embodiment of the invention, the accuracy can be improved to better than 0.5% using the density measuring device, or densitometer, depicted in FIG. 3. The densitometer 210 includes a pressure chamber 212, which provides for containment of a gas 13 in which a sample is immersed as some property of the gas 13, such as pressure of the gas 13, is varied. As shown in FIGS. 4A and 4B, the preferred embodiment of the pressure chamber 212 includes an outer cylindrical shell 213 and an inner body 214. During normal use, introduction and extraction of the sample from the interior of the chamber 212 is through a portal 258. For access to the balance or other interior elements, the chamber body 214 preferably slides out of the chamber shell 213. The chamber 212 is sealed with large O-rings fitting into O-ring grooves 265 in the chamber body 214. The chamber 212 of the preferred embodiment may be pressurized to at least 300 psi. However, with sufficient resolution it is possible to obtain measurement data from the device at lower chamber pressures.

As indicated in FIGS. 4A–4B, there are several measurement and control devices disposed in, or mounted to, the chamber 212 for measuring properties of the gas 13 and the sample inside the chamber 212, all of which are discussed in more detail below. The measurement and control devices include a weighing device 275 for determining the weight of the sample. The weighing device 275 of the preferred embodiment comprises a microbalance. However, it should be appreciated that the invention is not limited by the type of weighing device 275, which may be of a number of different types of load-measuring devices.

The weighing device 275 preferably includes a beam 295 as depicted in FIGS. 5A–5B. The beam balance 295 is the preferred apparatus for measuring the weight of samples, although considerable detail is required for a beam balance that is to operate with the desired sensitivity inside a pressure chamber. One of the most important considerations in the beam design is the location of the center of gravity and the moment of inertia for the beam 295. Specifically, the greatest sensitivity is achieved when the moment of inertia for the beam 295 is minimized, and the pivot point or fulcrum 345 is located very close to (but above) the center of gravity of the beam 295.

In attempting to make weight measurements at different gas densities, one must be vigilant with regards to how well the beam 295 is balanced in its design. First, it is desirable that the beam 295 be substantially balanced before any sample or calibration weight is applied to the beam 295. That is, force moments on opposing ends of the beam 295 should be substantially equal. Second, it is important that the beam 295 be balanced with respect to mass moments and volume moments. These two design considerations are described in detail hereinafter.

Figure 6:
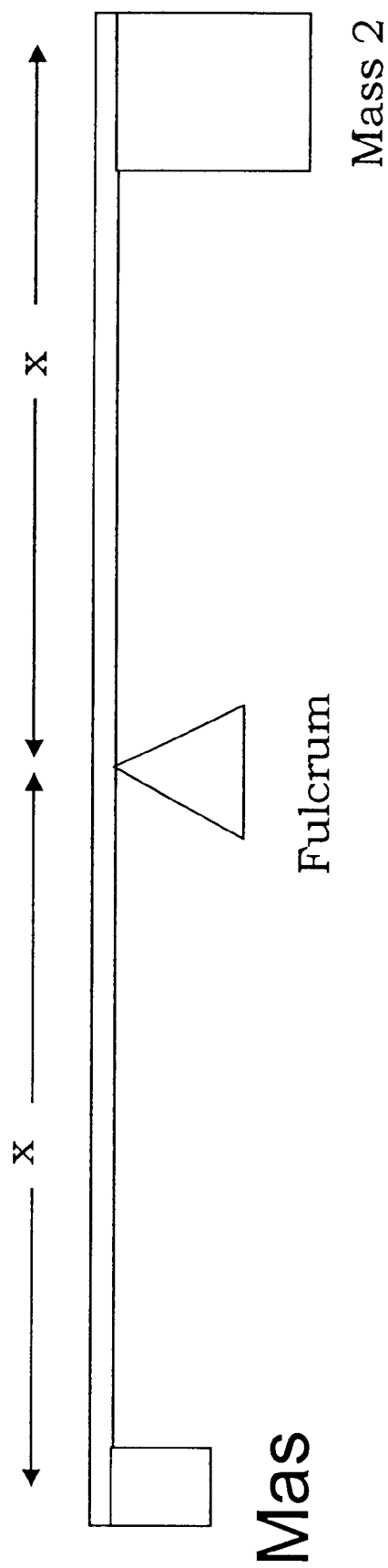
FIG. 6 depicts a beam balance according to a preferred embodiment of the invention.

Generally, the function of state-of-the-art beam balances is to measure the mass or weight of an object at substantially ambient conditions, i.e., ambient pressure, temperature, and humidity. Some of the more elaborate state-of-the-art beam balances used for traceable calibrations may be enclosed in a vacuum chamber to eliminate water vapor and buoyancy forces. In those devices, the preferred method of balancing the beam is to add mass to the beam to equalize the moments about the fulcrum. The moment in this case suggests the product of mass times distance from the fulcrum 345. Generally, the composition of the material in those masses which balance the beam are not a concern. FIG. 6 illustrates how a hypothetical beam might be balanced using equal masses of different composition. In a vacuum, the beam is balanced if the masses (Mass 1 and Mass 2) are equal and their distances (x) from the fulcrum are the same. However, if the beam is to remain balanced as a gas is pressurized around the weighing device, the simple arrangement shown in FIG. 6 would be a poor design. As the gas around the beam is densified, the right hand side of the balance in FIG. 6 experiences a greater buoyancy force than the left hand side due to the larger volume of Mass 2. Thus, additional force must to be added to the right hand side of the beam to keep the beam balanced.

In the preferred embodiment of this invention, it is most desirable to match the materials of the various components attached to each end of the beam. For example, to counteract the weight of the copper coil assembly 300 at one end of the beam 295, a position-adjustable copper counterweight 310 is applied at the opposite end of the beam 295.

In the preferred embodiment of the invention, as depicted in FIGS. 7A–7B, a sample pan 320 comprising a stainless steel foil cutout 321, a pan cross piece 323, a sample pedestal 324, and a flat sapphire window 322 rests on a sapphire knife edge 325 attached to the beam 295. Preferably, the sample pan 320 is constructed from a 0.010 inch thick stainless steel foil cutout 321, although other thicknesses would work as well. The cutout 321 is preferably photo etched from a larger sheet to obtain flat parts. The pan 320 is designed with a sapphire window 322 mounted with its flat surface perpendicular to the pan 320. The flat sapphire surface 322 rests on the knife edge 325 mounted on the beam 295. (See FIGS. 5A–5B.) A cross piece 323 disposed about halfway down the pan 320 is used for holding a tungsten calibration sample, and a sample pedestal 324 (preferably a 1 mm diameter stainless steel cylinder) is mounted at the bottom of the pan 321 as a rest for small samples. The knife-edge 325 of the preferred embodiment is manufactured by Delaware Diamond Knives (Wilmington, Del.) and is cut from a stock item used for microtomes.

A position-adjustable counterweight 330, preferably made of stainless steel, is applied to the opposite end of the beam 295 to counteract the combined weight of the pan 320, the pan cross piece 323, and the sample pedestal 324, and the sapphire window 322. Additionally, a sapphire window 350, which is substantially identical to the sapphire window 322, is applied to the end of the beam 295 opposite the knife edge 325 to counteract the weight of the sapphire window 322 of the pan 320 assembly. Thus, it is possible to equalize both the moments of mass about the fulcrum and the moments of volume about the fulcrum. Careful matching of the materials and their volumes results in the greatest sensitivity of the beam over large changes in gas density.

The most preferable design for the fulcrum to minimize sensitivity to vibration is one that utilizes ruby jewels 270 (FIGS. 4A and 4B) and hardened pivots 345 (FIGS. 5A and 5B) for the fulcrum. In the preferred embodiment, the jewels 270 and pivots 345 are commercial items (model numbers U-VJA-1 and VJPX-2D, respectively) provided by Small Parts of Miami Lakes, Fla. However, it will be appreciated that other structures may be used at the pivot point, such as a knife-edge.

In the preferred embodiment of the weighing device 275, balance counter force is applied by electromagnetic attraction to balance the system. As shown in FIGS. 5A–5B a coil assembly 300 (detailed in FIGS. 8A–8B) is affixed to the beam 295. As the beam 295 rotates about the pivot points 345 which rest in the jewels 270, the coil assembly 300 moves inside an annular magnet 216 (depicted in FIGS. 4A and 4B) without making physical contact with the magnet 216. The annular design of the preferred embodiment of the magnet 216 has at least two desirable characteristics. First, when the size of the gap between the magnet 216 and the coil assembly 300 is small, the flux lines are constrained to a small region in the gap, thereby eliminating the effects of ferrous materials moving in the vicinity of the densitometer 210. Second, by minimizing the size of the flux field relative to the coil dimensions, the force exerted on the coil assembly 300 is only a function of coil current, and not a function of the position of the magnet 216 in the magnetic field of the coil assembly 300.

To move the beam 295, an excitation current is provided by the closed loop controller 30 (FIG. 3) to the coil assembly 300, thereby producing an upward or downward force between the coil assembly 300 and the magnet assembly 216. Preferably, the closed-loop-controller is constantly adjusting the coil current to maintain the beam 295 in a balanced position. During operation of the densitometer 210, the coil current required to keep the beam 295 balanced is monitored with and without samples on the pan assembly 320 by the data acquisition board 48 which is coupled to the processing unit 46 of the computer 35.

Figure 8B:
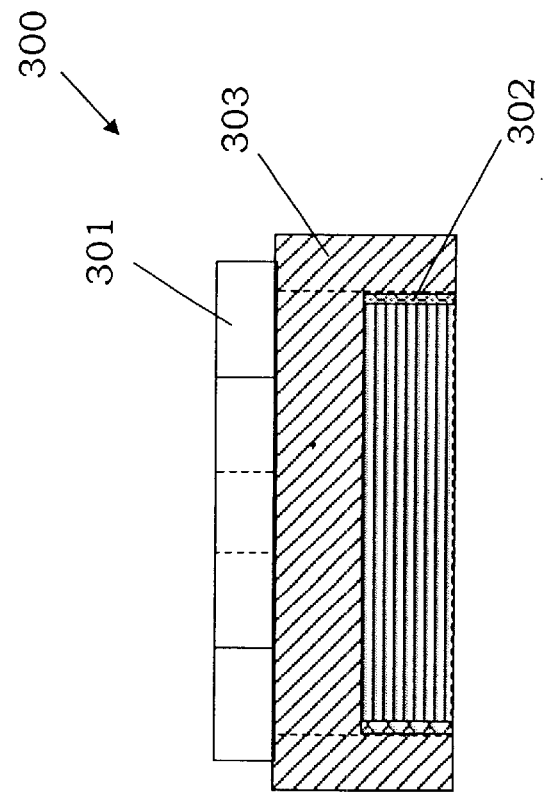
FIGS. 8A–8B depict two views of a coil assembly according to a preferred embodiment of the invention.
Figure 8A:
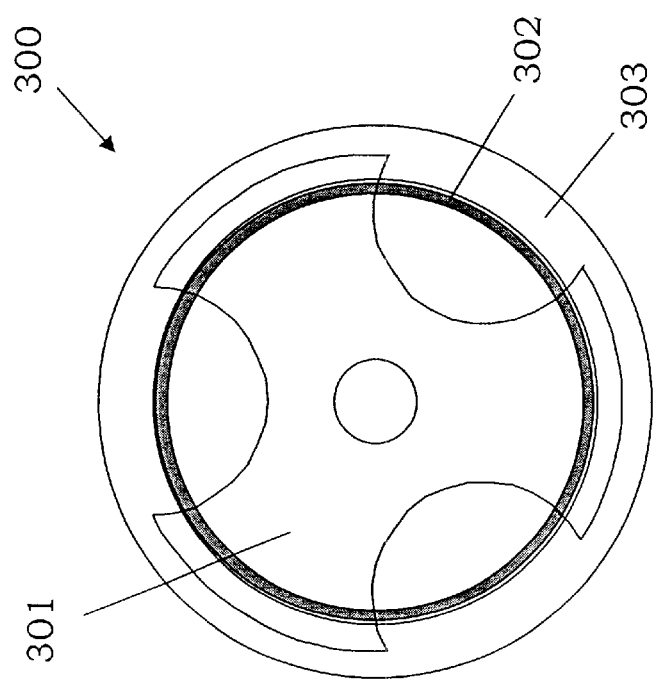

As shown in FIGS. 8A–8B, the preferred embodiment of the coil assembly 300 consists of a coil plate 301, a coil 302, and a magnetic damping ring 303. The coil plate 301 is a structural element comprising a thin copper plate chemically etched from a copper foil. The coil plate 301 is preferably screwed or bonded by other agents, such as epoxy, to the beam 295. Affixed to the coil plate 301 is the magnetic damping ring 303, which is preferably formed from aluminum. Those skilled in the art will appreciate that when such a ring is moved within a magnetic field, such as exists in the gap of the annular magnet 216, an electrical current is produced in the damping ring 303. The current in the damping ring 303, which is in the magnetic field of the annular magnet 216, produces a force that resists the motion of the magnetic damping ring 303. Thus, the magnetic damping ring 303 provides a dampening effect on the beam 295, thereby minimizing oscillation of the beam 295 from the closed loop controller 30.

Since the weighing device 275 of the preferred embodiment is enclosed within the solid metal chamber 212, it is difficult to visually determine when the beam 295 is balanced. Preferably, as depicted in FIGS. 3, 4A–4B, and 9, the electronic closed-loop-controller 30 keeps the beam 295 in balance utilizing a position detector system comprising a light emitting device 225 and a light detection device 227. The position detector system of this preferred embodiment operates over a range of gas densities while eliminating some unintentional adverse effects of prior embodiments. In prior embodiments of the invention, two emitter-detector pairs were used to determine position, preferably at opposite ends of the beam. In that design, it was possible for different combinations of position and alignment of the two sets of emitters and detectors to yield the same signal output. That is, a poorly aligned emitter/detector pair close to the beam could provide the same level of signal output as a well aligned emitter/detector pair further away from the beam. Thus, as gas pressure increases, the output of the two detectors may not change in the same manner as the gas scatters the light from the emitters.

Figure 9:
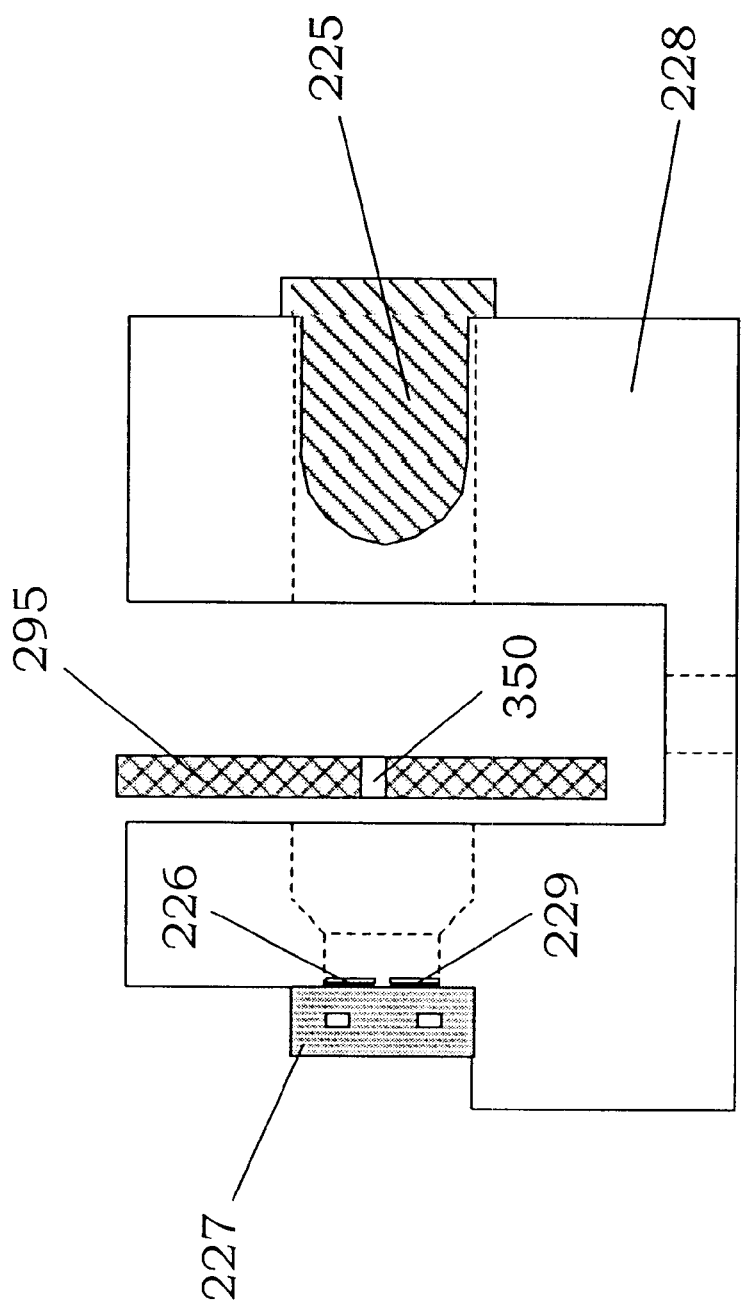
FIG. 9 depicts an optical emitter/detector assembly according to a preferred embodiment of the invention.

In the preferred embodiment, as depicted in FIG. 9, the emitter 225 is a red light emitting diode (LED) attached to an LED mount 228. However, it will be appreciated that other light sources could be used. The LED is preferably powered with a constant current source associated with the closed-loop-controller 30. The emitter 225 is oriented such that the light emitting from the LED 225 is directed at the detector 227. The detector 227 of this embodiment is a two-element photodiode array manufactured by Hamamatsu under model S4204 consisting of two 1 mm square silicon devices 226 and 229 attached to the LED mount 228 and separated by a 20 micron gap. The split diode is more preferred as it eliminates problems associated with prior embodiments by reducing the number of light paths from two to one. As shown in FIG. 9, the detector 227 is preferably a dual inline package (DIP) for ease of electrical connection. Although the greatest sensitivity of the detector 227 is in the infrared regime, it should be appreciated that emitters 225 of other wavelengths could be used. It should also be appreciated that other types of detectors 227 could be used.

As depicted in FIG. 9, the beam balance 295 with a 0.5 mm wide slit 350 is disposed between the LED 225 and the detector 227. The slit 350 moves up and down as the beam 295 pivots about its fulcrum 345. Thus, if the beam 295 were to move down, for instance, the light beam from the LED 225 passing through the slit 350 falls more on the bottom diode element 229, and if the beam rotates in the opposite direction the light beam falls more substantially on the top diode element 226. When the beam 295 is exactly balanced, the light intensity measured by the two silicon diode elements 226 and 229 will be substantially equal. Thus, the difference between the signal outputs of the two diode elements 226 and 229 determines how far the beam 295 is from its balanced position. This difference between the outputs of the detectors 226 and 229 is referred to herein as the error signal.

Within the controller 30, the error signal preferably passes through a proportional-integral-differential (PID) control loop and is amplified. Those skilled in the art of control theory will appreciate the purpose of the proportional, integral, and differential elements of a PID control loop. The output of the PID loop is sent through a sensing load resistor (also preferably in the closed-loop-controller 30), as a means for measuring the current in the coil 302. The voltage drop across the sensing load resistor, which is proportional to the current and the resistance of the load resistor, is provided to the data acquisition board 48, and is measured as a representation of the electromagnetic force required to make the output of the two detector elements 226 and 229 substantially equal.

Generally, the output of the LED 225 does not change from ambient pressure to elevated pressure. However, the light intensity received at the detectors 226 and 229 does change with gas density due to scattering by gas molecules. Using the dual-diode detector 227, the intensity incident on each element 226 and 229 of the photodiode 227 is reduced equally. Thus, the current output of each diode 226 and 229 may be reduced at elevated pressures from that at ambient pressure, but when the light intensity is reduced by the same amount on the two elements 226 and 229, the beam 295 will still be balanced. That is, the slit 350 on the beam 295 is still centered over the gap between the two light sensing elements 226 and 229.

With reference to FIG. 3, the densitometer 210 includes a pressure transducer 232 for measuring gas pressure within the chamber 212. In the preferred embodiment, the pressure is measured using a model 4040 or 6000 device manufactured by Mensor Corporation of San Marcos, Tex. The 4040 model has a precision and accuracy of 0.003% and 0.01%, respectively, while the 6000 model transducer has a precision and accuracy of 0.006% and 0.02%, respectively. These characteristics are multiplied by the full-scale range of the device to obtain the absolute accuracy and precision of the pressure transducer 232. Preferably a pressure transducer 232 with an absolute pressure range from 0 to 300 psia is used, such that the precision and accuracy of the 4040 model is 0.01 psi and 0.03 psi, respectively.

Preferably, the transducer 232 includes an RS-232 output which allows the computer 35 to directly capture the pressure in PSI without using any calibration constants in the software. The Mensor devices described above are fully calibrated and provide the signal in PSI directly. Thus, when the software is controlling the densitometer, a request for a pressure value is sent via the RS-232 bus to the pressure transducer and a pressure measurement in psi units is returned.

In the preferred embodiment, temperature is measured using a thermistor 236 rather than a thermocouple. The thermistor 236 is an electronic device that changes resistance with temperature, and is extremely accurate over a temperature range that includes typical room temperatures. The preferred thermistor 236 has a resistance of 10 KΩ at 25° C. and has a resistance change of approximately 400 Ω/degree C. With an appropriate signal conditioner 238 and data acquisition system 48, tremendous precision (0.001° C.) and accuracy (0.01° C.) can be achieved.

In the preferred embodiment, the temperature signal conditioner 238 includes a 15 volt regulated power supply, although a regulated power supply providing less or more voltage could be used. Most of the voltage is dropped across a precision load resistor with a low thermal coefficient (approximately 20 ppm/° C.). The load resistor is used to reduce the convenient 15 volt supply to approximately 1.8 volts going into the thermistor resistance bridge. The desired effect of reducing the bridge voltage is to reduce the bridge current, which could result in undesired heating of the thermistor 236. Those skilled in the art will understand the theory and application of resistance bridges, so only a brief description is given here. The remaining voltage dropped over a resistance bridge where one of the four legs is the thermistor 236. The remaining three legs of the bridge are preferably precision 10 KΩ resistors with low thermal coefficients (approximately 20 ppm/° C.).

The output voltage of the bridge provides an indication of the temperature at the location of the thermistor 236, which resides inside the chamber 212 near the beam 295. The output voltage is preferably measured by the computer 35 in the following manner. The two output points of the resistance bridge are used as inputs to a precision instrumentation amplifier, such as a model AD621 manufactured by Analog Devices, the internal gain of which is preferably set to ten. The output of the instrument amplifier is then filtered through a low-pass filter using a resistor and capacitor to reduce the high frequency noise typical of electronic systems. The output of the instrument amplifier and a "local" ground signal are sent to the data acquisition board 48, such as a model PCI-6036E board manufactured by National Instruments. The two input signals are used with one differential input channel on the board 48. The data acquisition board 48 is preferably capable of reading up to 200,000 samples/sec, but is typically run closer to 100,000 samples per second. A typical reading used in the software uses 20,000 samples of data.

Calibration of the thermistor 236 and the signal conditioner 238 is preferably accomplished by comparing the voltage measured by the data acquisition board 48 with the reading on a glass mercury thermometer, such as manufactured by Omega Engineering (accuracy 0.01° C.). Both the calibration device and the thermistor are held at substantially the same temperature inside an air-filled calibration chamber constructed of aluminum and immersed in a water tank of changing temperature. The relationship between the reading on the mercury glass thermometer and the electronic signal is used as the temperature calibration, thereby yielding an accuracy of 0.01° C.

In an especially preferred embodiment, commercially-available devices are used to electronically control the pressure inside the chamber. In such an embodiment, the pressure regulator 40 controls the chamber pressure based on a proportional input signal, such as provided by the computer 35. The regulator of this embodiment includes two solenoid-activated valves that are operated by an active control loop within a controller integral to the regulator 40. One solenoid opens a vent valve to the atmosphere if the chamber pressure exceeds a maximum pressure, and the other solenoid opens a valve to a high pressure gas tank 42 when the chamber pressure drops below a minimum pressure.

In an alternative embodiment, the gas distribution system consists of a mechanical regulator 40 mounted on the gas tank 42 having a pressure control knob 41 and a needle valve 43. Down stream of the mechanical regulator 40 is a solenoid valve 250 that is either open or closed and is used to either purge the chamber 212 or pressurize the chamber 212. On the output side of the chamber 212 is a second solenoid valve 215 that allows the chamber 212 to be purged, or depressurized. The data acquisition board 48 connected to the computer 35 uses a logic signal to provide power to the solenoid valves 215 and 250. When the chamber 212 is to be purged, both solenoids 215 and 250 are opened by software control. When the software program needs to reduce the gas pressure the solenoid 215 is opened. When pressurizing the chamber 212, the solenoid valve 250 is opened by software control.

As shown in FIG. 3, the computer 35 preferably includes a processing unit 46, the data acquisition board 48, a hard drive 50, a keyboard 52, and a monitor 54. In a preferred embodiment, the data acquisition board 48 has multiplexing capability, such as provided by the model PCI-6036E manufactured by National Instruments, for receiving the temperature signal from the temperature signal conditioner 238, the pressure signal from the pressure transducer 232, and the coil voltage from the closed loop controller 30, and for converting these analog signals to corresponding digital signals.

The hard drive 50 provides for storage of calibration constants and measured data. As discussed in more detail below, the calibration constants pertain to the properties of the gas 13, the voltage-to-temperature relationship for the thermistor 236, and the output of the pressure transducer 232.

During operation of the densitometer 210, measured values include voltage signals corresponding to the pressure and temperature of the gas 13 in the chamber 212, the apparent weight of the sample, and time. Although pressure and temperature are not variables in equations (5) or (6), these properties may be used to determine the density of a gas of known species and purity. Hexafluorethane ($C_2F_6$) is chosen as the preferred gas 13 for use in the densitometer 210 since it has a very high density relative to other gases. By use of the ideal gas law (and corrections to it at elevated pressures), the actual density of the $C_2F_6$ gas 13 may be calculated based on the internal pressure and temperature in the chamber 212. Details of the calculation of gas density based on pressure and temperature is described in more detail below.

Figure 10A:
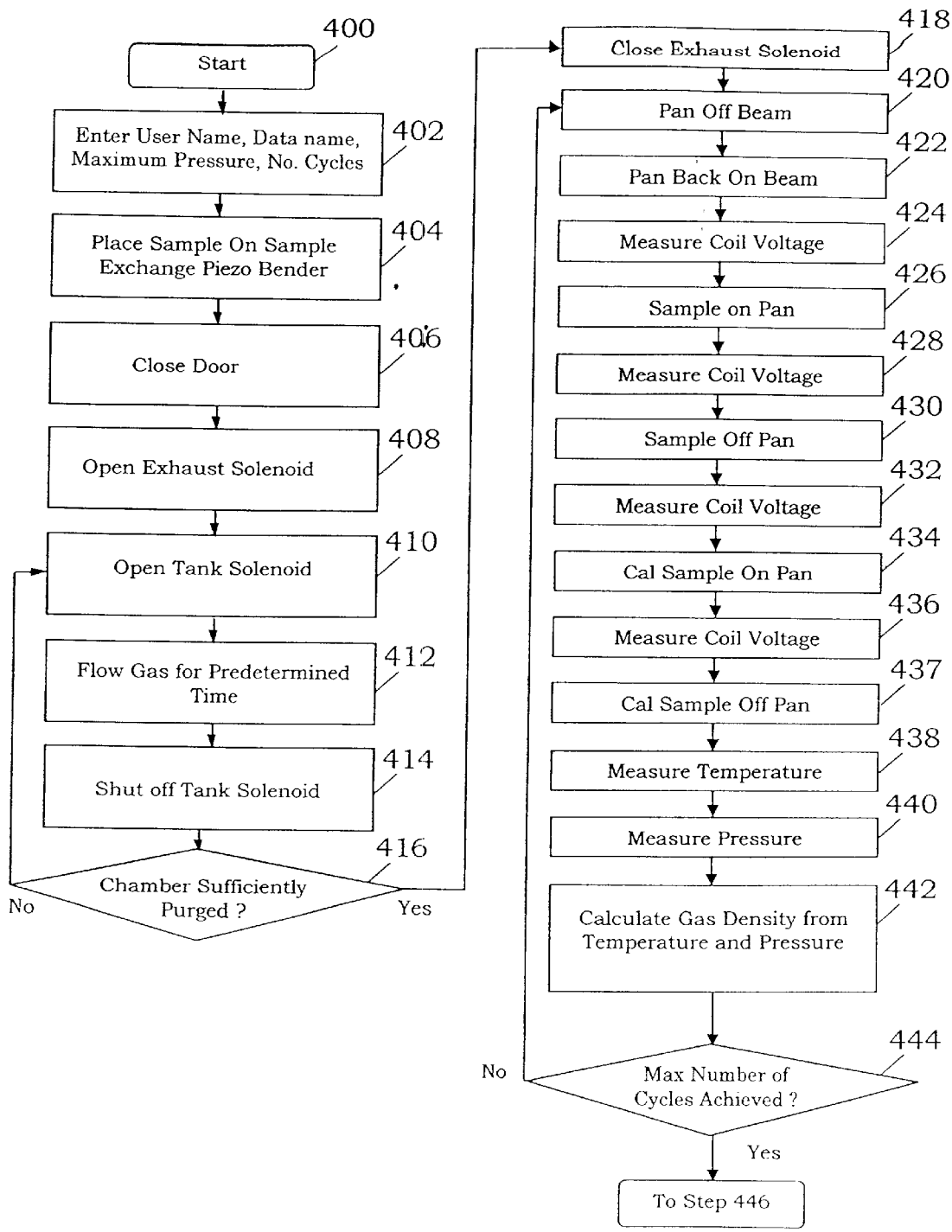
FIGS. 10A–10B depict a functional flow diagram for a method for determining density of a sample according, to a preferred embodiment of the invention.
Figure 10B:
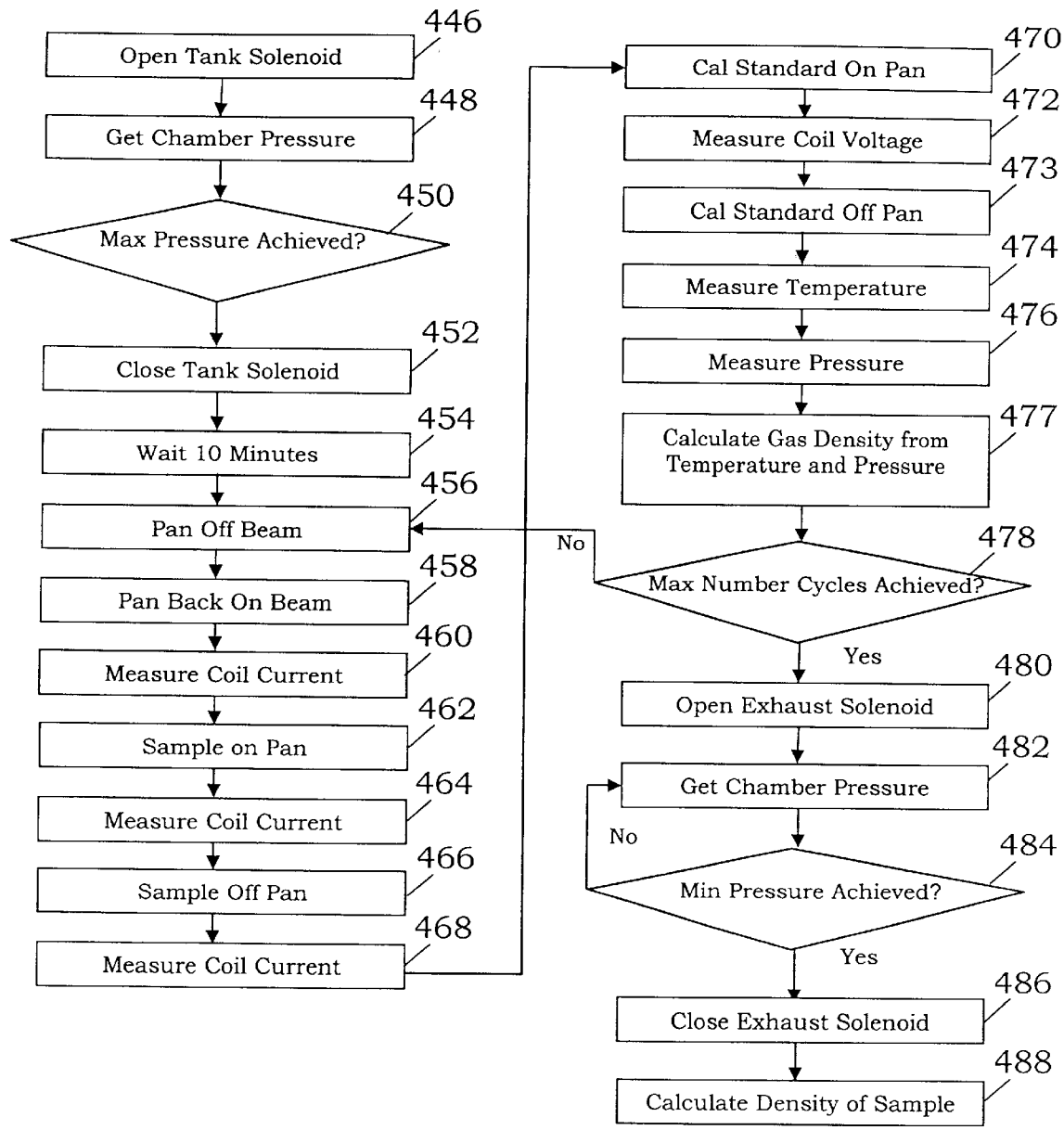

Referring to FIGS. 10A–10B, the step-by-step operation of the densitometer 210 according to the preferred embodiment of the invention is next described. In this preferred embodiment, the densitometer 210 is controlled by the computer 35, and data is logged by the processing unit 46 using software instructions contained within one or more software programs.

To begin a test, a test operator begins execution of the software program (step 400) and follows prompts and requests provided by the program via the monitor 54. Preferably, the operator enters, via the keyboard 52, the operator's name, a unique identifier for the test, the maximum gas pressure, the number of purge cycles, and the number of measurement cycles (step 402). The unique identifier for the test is preferably stored with the data so that the data can be easily retrieved at later time. In an alternative embodiment that includes a voltage-controlled pressure regulator, the operator creates or selects a pressure-time schedule at step 402 for the pressure in the chamber 212 to follow during the test.

Figure 11A:
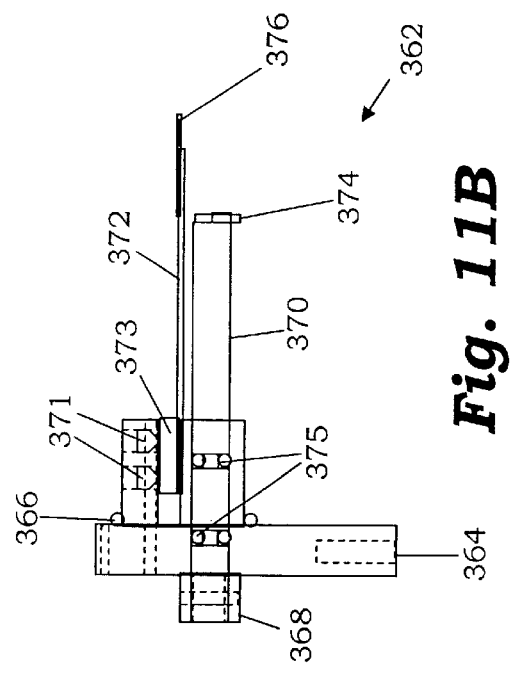
FIGS. 11A–11C depict three views of a door assembly for a gas chamber according to a preferred embodiment of the invention.
Figure 11B:
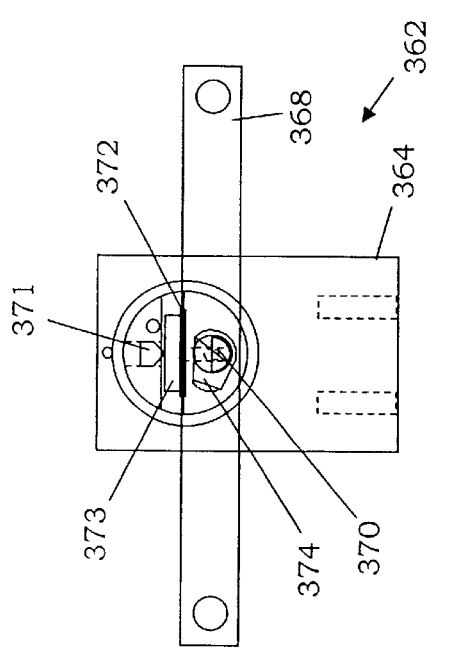
Figure 11C:
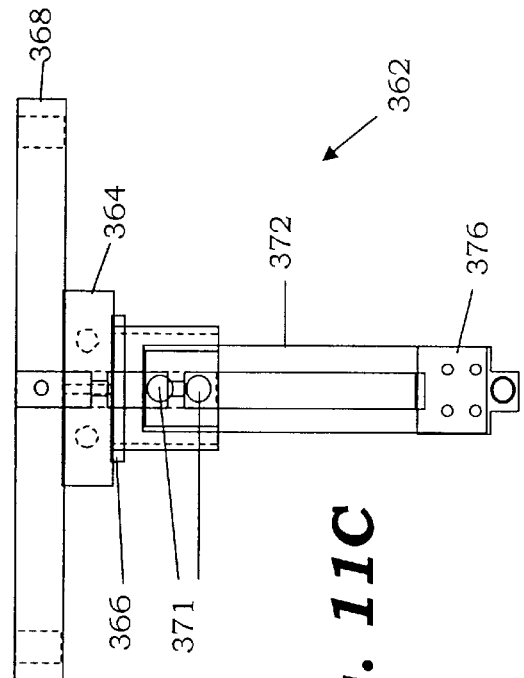

With reference to FIGS. 4A–4B and 11A–11C, a sample 355 is placed manually on the sample holder 376 of the chamber door assembly 362 (step 404), and the removable door 364 of the chamber 212 is replaced and secured (step 406). The door assembly 362, as depicted in FIGS. 11A–11C, includes a door 364, an o-ring seal 366, a door latch 368, a piezo rod 370, a piezo bender 372, a cam 374, and a sample holder 376. In the preferred embodiment, the piezo rod 370, the cam 374, and the door latch 368 turn together such that the piezo bender 372 is pushed up away from the sample pedestal 324 (FIG. 7A–7A) when the door 364 is being opened and closed. The piezo rod 370 is outfitted with two small O-rings 375 to prevent gas from leaking along the interface between the piezo rod 370 and the door 364. The piezo bender 372 is secured to the door 364 with two conical set screws 371 and a soft polymer pillow 373.

The program pauses through the sample introduction step 404 and waits until the door is closed (step 406). The program resumes when the user clicks an "OK" button in the software indicating that the sample has been introduced and the door assembly 362 is closed. From this point forward the operation is completely independent of the user and is completely operated by the computer 35.

The chamber vent valve 215 (FIG. 3) is opened (step 408), and a second solenoid valve 250 is opened to allow the gas 13 to run into the chamber 212 from the high-pressure tank 42 via the mechanical pressure regulator 40 (step 410). The gas is allowed to flow for a predetermined time flushing the chamber 212 of unwanted air and replacing with $C_2F_6$. At the end of the time segment the tank solenoid 250 is closed (step 414) and is followed by a 15 second wait. This process, as indicated at steps 410–416 of FIG. 10A, is repeated a predetermined number of times (entered at step 402). Note that the purge pressure is selected arbitrarily and the number of purge cycles may be variable; thus, the purging process could be accomplished at other pressures and other numbers of cycles.

The exhaust solenoid 215 is closed and the system begins to make weight measurements at ambient pressure in the $C_2F_6$ by the following procedure. Preferably, the weighing device 275 has a mechanism for realigning the pan assembly 320 on the knife edge 325 that is affixed to the beam 295. That mechanism, which is preferably a piezo bender 256 as shown in FIGS. 4A–4B, physically picks up the pan assembly 320 by two outer tabs 328 on the pan 321 (step 420). Preferably, the bender 256 is actuated such that it bends through its maximum deflection of 2 mm over approximately 10 seconds. After a program pause of roughly 15 seconds the pan is replaced on the beam by bending the piezo bender 256 in the opposite direction (step 422). After a wait of approximately 1 minute, the current provided to the coil 302 is measured by the data acquisition unit 48. As previously described the coil current is determined by measuring the voltage drop across a precise load resistor in the PID loop of the closed-loop-controller 30 (step 424). This coil current represents a "zero" or "null" for the balance.

Once a steady measurement of the coil current ha been obtained, the sample 355 is placed on the sample pedestal 324 of the pan assembly 320 (step 426). When the door assembly 362 was secured to the rest of the chamber 212 (step 406), the sample holder 376 holding the sample 355 was positioned directly above the sample pedestal 324. Thus, when the sample piezoelectric bender 372 is actuated by the program control, the sample weight is applied to the pan assembly 320. The closed-loop-controller 30 actively finds the required coil current required to keep the beam 295 balanced with the added sample weight 355 on the pan assembly 320. This coil current is measured (step 428) and is a representation of the sample weight. After the coil current measurement is completed, the sample piezoelectric bender 372 is activated in the opposite direction removing the sample 355 from the sample pedestal 324 of the pan assembly 320 (step 430).

A second measurement of the "zero" or "null" weight is determined by again measuring the coil current (step 432). This second measurement determines whether anything has shifted during the first two coil current measurements (steps 424 and 428). The calibration, sample is then placed on the pan cross piece 323 (FIG. 7A–7B) by activating a third piezo bender 257 (step 434). The calibration sample is preferably a high purity tungsten foil 0.004 inches thick which is cut in the shape of a circle with a diameter of 0.28 inches. The calibration sample normally resides within the chamber 212 and is inaccessible by the user. The coil current is measured by the voltage drop across the load resistor in the closed-loop-controller 30 and is a representation of the calibration standard weight (step 436). The calibration standard is then removed from the pan cross piece 323 by activating the piezo bender 257 in the opposite direction (step 437).

As stated previously, there are preferably three measurements that are made by the system during a test: the weight, the gas temperature, and the gas pressure. Just described in steps 420 through 437 was the method of weighing the pan, the sample, and the calibration standard. Next the program running in the processing unit 46 determines the gas temperature (step 438), preferably by making 20,000 voltage measurements across the resistance bridge in the temperature signal conditioner 238 at a rate of 100,000 samples per second. The voltage measurement is converted immediately to a temperature through a temperature calibration, previously discussed. Finally, the gas pressure is determined (step 440) through a serial port by requesting a pressure from the pressure transducer 232. All five measurements are transferred to the hard drive 50 connected to the computer 35.

At step 442, the program calculates gas density from gas pressure and temperature measurements (steps 438 and 440). At low pressures and temperatures, most gases behave "ideally", that is, the pressure, temperature, and density are all related through a linear relationship called the ideal gas law, which is expressed by:

$$PV=nRT, \qquad (12)$$

where P is the pressure, V is volume, n is the number of moles of gas, R is the gas constant, and T is the absolute temperature. Since the ratio n/V can be thought of as a measure of gas density, P is linearly proportional to density at a constant temperature. At higher pressures, though, the ideal gas law needs to be modified to accurately express the relationship.

Figure 12:
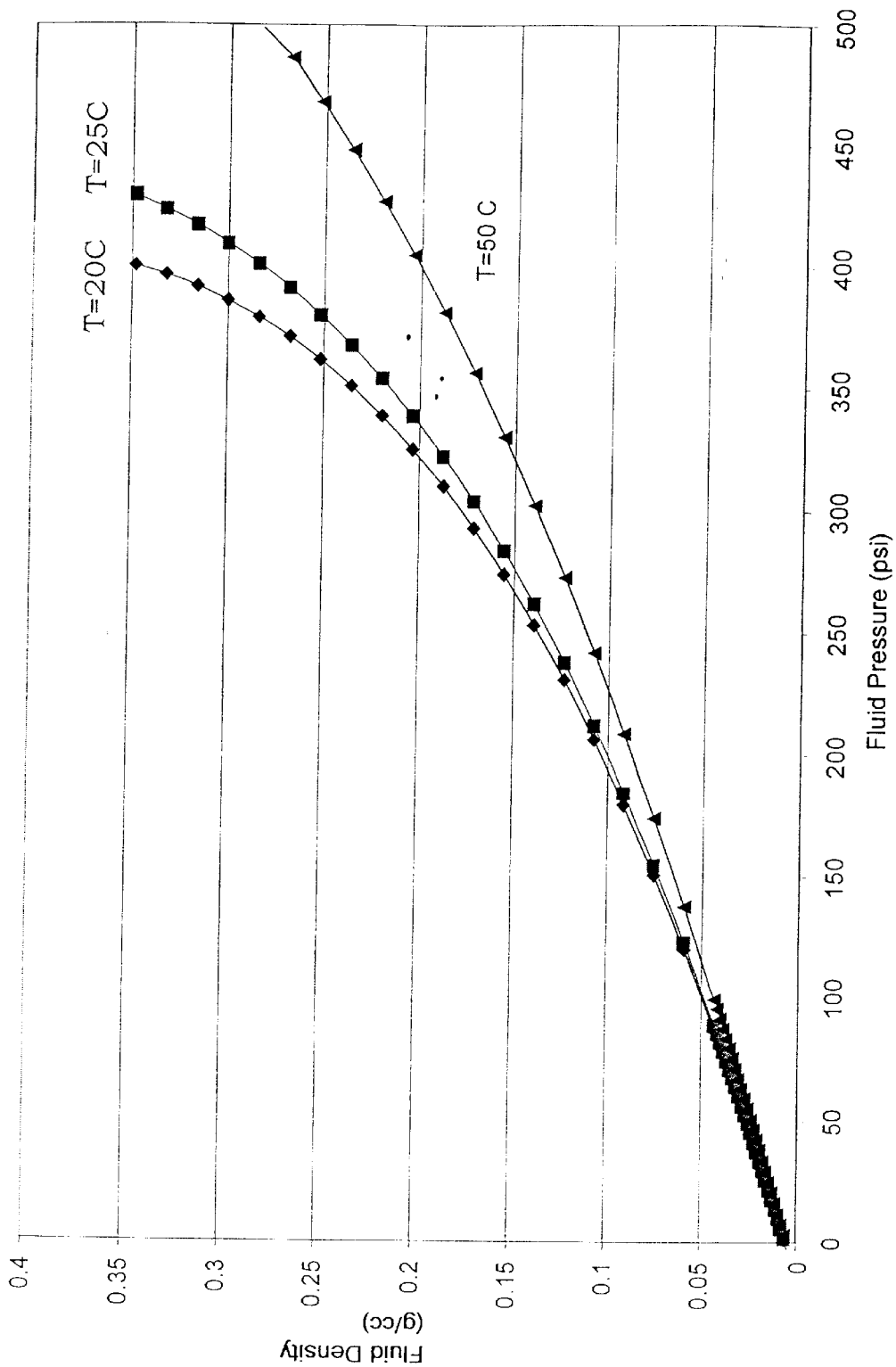
FIG. 12 depicts a graphical relationship between fluid density, fluid pressure, and temperature for a particular gaseous medium.

The densitometer 210 of the present invention operates at pressures as high as 300 psi, where the actual behavior of $C_2F_6$ deviates from the ideal gas law. An equation of state that more accurately expresses the relationship between pressure, temperature, and density for $C_2F_6$ over the range of pressures in which the invention operates is found in "Thermophysical Properties of Gaseous $CF_4$ and $C_2F_6$ from Speed-of-Sound Measurements," by J. J. Hurly, published in the International Journal of Thermophysics, Vol.20, No.2, 1999. This relationship, which is represented graphically in FIG. 12 for gas temperatures of 20° C., 25° C., and 50° C. is used by the program to calculate gas density (step 442). As FIG. 12 indicates, $C_2F_6$ behaves somewhat ideally at low pressures where the relationship between density and pressure is nearly linear. However, at pressures above about 150 psi, the relationship begins to deviate from the linear behavior, requiring use of the more accurate equation of state as provided by the Hurly reference. The curves also suggest that a temperature dependence becomes significant at pressures greater than roughly 300 psi. The calculated gas density is stored on the hard drive 50 with the other acquired data.

The steps of measuring the pan weight, sample weight, calibration standard weight, and gas density are repeated (step 444) a number of times predetermined in step 402. Once the predetermined number of data sets are acquired, the program opens the solenoid valve 250 and pressurizes the chamber 212 to a predetermined value from step 402 (step 446). As the pressure in the chamber 212 increases, the program continues to monitor the internal pressure of the chamber 212 by querying the pressure transducer 232 (step 448). After each pressure measurement (step 448) the question is asked whether the maximum desired pressure has been reached (step 450). If the system has not achieved the maximum pressure, it returns to make a new pressure measurement. If the measured pressure exceeds the desired maximum pressure, the tank solenoid 250 is closed (step 452). The program then pauses for a predetermined time, such as 10 minutes, to allow the gas and parts of the weighting device to thermally stabilize (step 454). It is typical that the temperature of the chamber can change by one or two degrees Celsius during the pressurizing and depressurizing steps. The pause ensures that the gas has a constant temperature, and hence, a constant density throughout the chamber 212.

In steps 456 through 478, the same set of weight measurements are made as in steps 420 through 444. The pan piezo bender (256) is actuated to lift the pan assembly 320 from the knife edge 325 (step 456). After a program pause of roughly 15 seconds the pan is replaced on the beam by bending the piezo bender 256 in the opposite direction (step 458). After a wait of approximately one minute, the current provided to the coil 302 is measured by the data acquisition unit 48. As previously described, the coil current is determined by measuring the voltage drop across a precise load resistor in the PID loop of the closed-loop-controller 30 (step 460). This coil current represents a "zero" or "null" for the balance at high gas density.

Once a steady measurement of the coil current has been obtained, the sample 355 is placed on the sample pedestal 324 of the pan assembly 320 (step 462). The closed-loop-controller 30 actively finds the required coil current required to keep the beam balanced with the added sample weight 355 on the pan assembly 320. After a 60 second program pause, this coil current is measured (step 464) as a representation of the sample weight. After the coil current measurement is completed, the sample piezo bender 256 is activated in the opposite direction removing the sample 355 from the sample pedestal 324 of the pan assembly 320 (step 466).

After waiting approximately 60 seconds, a second measurement of the "zero" or "null" weight is determined by again measuring the coil current (step 468). This second measurement determines whether anything has shifted during the first two coil current measurements (steps 460 and 464). The calibration standard is then placed on the pan cross piece 323 by activating the third piezo bender 257 (step 470). The coil current is measured (step 472) by the voltage drop across the load resistor in the closed-loop-controller 30 as a representation of the calibration standard weight. The calibration standard is then removed from the pan cross piece 323 by activating the piezo bender 257 in the opposite direction (step 473).

Similar to the cycles at ambient pressure, the gas temperature (step 474) and the gas pressure (step 476) are measured and stored with each set of weight measurements. Using the equation of state and the measured temperature and pressure the gas density corresponding to each cycle is also determined. The steps of measuring the pan weight, sample weight, calibration standard weight, and gas density are repeated (steps 456–477) a number of times, as predetermined in step 402 (step 478).

Once the predetermined number of data sets are acquired at high pressure, the program opens the exhaust solenoid valve 215 and depressurizes the chamber 212 to a predetermined value provided at step 402, which is usually ambient pressure (step 480). As the pressure in the chamber 212 decreases, the program continues to monitor the chamber pressure via the pressure transducer 232 and compares with the target pressure (steps 482 and 484). When the desired pressure is attained, the program closes the exhaust solenoid valve 215.

In the preferred embodiment of the invention, program execution now proceeds to calculating the density of the measured sample based on the measurements described above. The following describes how the calibration standard is used, and how equation (6) is used to determine sample density.

Prior electronic beam balances required a calibration standard if one was to measure the weight of a sample explicitly. That is, an electronic measure of the weight of the sample pan was made without the sample or calibration standard. This signal effectively "nulled" or "zeroed" the system. The sample was then placed on the weighing device and a second measurement of the output signal was made. A third measurement was required to determine the load calibration of the instrument, i.e., the relationship between force and voltage. Due to thermal drift in the electronics, or thermal expansions in the apparatus, the force calibration of the apparatus could drift with time. Thus, a calibration weight of very precise and accurate known weight was applied to the apparatus to obtain this third measure of the output signal. Effectively, the weight of the sample was obtained relative to the known weight of the calibration standard.

Although the present invention incorporates a calibration standard, its purpose is different than that of prior balances whose objective was to measure weight explicitly in force units. This difference is described in more detail below.

There are assumptions that have been made to this point in the use of equation (6). First, it has been assumed that the forces used in equation (6) do not need to be measured explicitly. That is, if the forces are equal to a measured coil voltage times a force calibration constant (v times C), the force calibration constant cancels out of the four terms in equation (6). Second, and subordinate to the first is the assumption that the force calibration constant, C, is the same at low and at high pressures. In prior density measurement devices, this latter assumption introduced error to the sample density measurement. The method of using the calibration standard of the present invention eliminates the error inherent in prior systems wherein the density of a gas is changed around the weight measurement apparatus. The inventors of the present invention have determined that the force constant does change slightly in going from ambient pressure to high pressure, and the preferred embodiment of the invention compensates for that change. Although the present invention is not limited to any particular theory of operation, it is believed that the magnetic susceptibility of the gas changes as a function of gas density, thereby effectively changing the force constant.

The procedures for using the calibration sample according to the preferred embodiment are discussed next. As mentioned above, the calibration standard is preferably a 99.95% pure tungsten foil 0.004 inches thick and 0.28 inches in diameter. The foil of the preferred embodiment was provided by Alfa Aesar of Ward Hill, Mass. Although the size is arbitrary, it is desirable that it is a large fraction of the load range of the apparatus. The material is also arbitrary, although it must be of known density, since it is being used as a calibration material.

As described above, during operation of the invention, the sample of unknown density and the calibration standard are weighed alternately. Under computer control, the apparatus nulled the system by measuring the coil voltage with neither the sample nor the calibration standard on the pan.

The function of the calibration standard is to determine precisely how much the force constant has changed between the first pressure measurement and the second pressure measurement. Examination of equation (6) reveals the usefulness of the calibration standard. Equation (6) can be rewritten as $$\rho_o = \frac{v_{a1} C_1 \rho_2 - v_{a2} C_2 \rho_1}{v_{a1} C_1 - v_{a2} C_2}, \quad (13)$$

where $C_1$ and $C_2$ are the force calibrations at the first and second pressures. Note again that if $C_1$ is equal to $C_2$, they cancel out of the equation and the sample density is measured as a function of coil voltage and gas density only. As discussed above, the gas density is determined based on measurements of the gas temperature and gas pressure. Interestingly, one does not need to know $C_1$ or $C_2$ explicitly to determine the sample density. Rather, all that need be known is the change in the force constant. Dividing the top and bottom of equation (13) by $C_2$, the expression can be rewritten as $$\rho_o = \frac{v_{a1}(C_1/C_2)\rho_2 - v_{a2}\rho_1}{v_{a1}(C_1/C_2) - v_{a2}}. \quad (14)$$

Solving equation (14) for the ratio of $C_1/C_2$ yields the following expression:

$$C_1/C_2 = \frac{v_{a2}(\rho_0 - \rho_1)}{v_{a1}(\rho_0 - \rho_2)}. \quad (15)$$

Since the density of the tungsten calibration standard is known, equation (15) maybe solved to determine the ratio $C_1/C_2$ according to:

$$C_1/C_2 = \frac{v_{a4}(\rho_C - \rho_1)}{v_{a3}(\rho_C - \rho_2)}, \quad (16)$$

where $\rho_C$ is the density of the calibration standard (19.3 g/cc for tungsten), $\rho_1$ is the first density of the gaseous medium as determined from the equation of state, $\rho_2$ is the second density of the gaseous medium as determined from the equation of state, $v_{a3}$ is a voltage related to the coil current required to balance the beam 295 at the first gas density, and $v_{a4}$ is a voltage related to the coil current required to balance the beam 295 at the second gas density.

Once the ratio of $C_1/C_2$ is known, equation (14) may be solved to determine the unknown density of the sample. As described above, according to the preferred embodiment of the invention, the calibration standard is measured and the $C_1/C_2$ ratio is calculated with every test.

Some example cases are discussed next.

CASE 1: Copper
    Approximate dimensions: 3 mm diameter disk, 0.25 mm thick
    Number of cycles: 5
    Average measurements from ambient pressure (14.727 psi)
        Average Null Voltage 1: 9.1399 volts
        Average Sample Voltage: 5.6834 volts
        Average Null Voltage 2: 9.1400 volts
        Average Calibration Weight Voltage:−6.7261 volts
        Average Gas Density: 0.0058 g/cc
    Average measurements from High Pressure (248.987 psi)
        Average Null Voltage 1: 7.8195 volts
        Average Sample Voltage: 4.4158 volts
        Average Null Voltage 2: 7.8197 volts
        Average Calibration Weight Voltage:−7.9146 volts
        Average Gas Density: 0.1230 g/cc The weight of the calibration standard is determined, in volts, from the difference between the average null voltage 2 and the average calibration weight voltage at both ambient and high pressure. Thus, the voltages $v_{a1}$ and $v_{a2}$ in equation (14) are 15.8661 volts and 15.7343 volts, respectively, for ambient and high pressure. Thus, in this example, $C_1/C_2$= 0.997755.

The unknown density of the sample is now be determined using equation (14) and the known ratio of $C_1/C_2$. The weight of the sample is determined, in volts, from the difference between the null voltage 1 and the sample voltage at ambient and high pressure. Thus, the voltages $v_{a1}$ and $v_{a2}$ for equation (14) are 3.4565 volts and 3.4037 volts, respectively for ambient and high pressure. Using the ratio $C_1/C_2$ determined with the tungsten calibration standard, the density of the sample is determined to be 8.95 g/cc, which compares well with the theoretical value of 8.94 g/cc.

CASE 2: Aluminum
    Approximate dimensions: 3 mm diameter disk, 0.48 mm thick
    Number of cycles: 5
    Average measurements from ambient pressure (14.790 psi)
        Average Null Voltage 1: 9.1346 volts
        Average Sample Voltage: 7.1830 volts
        Average Null Voltage 2: 9.1346 volts
        Average Calibration Weight Voltage:−6.7249 volts
        Average Gas Density: 0.0058 g/cc Average measurements from high pressure (248.819 psi)
Average Null Voltage 1: 7.8094 volts
Average Sample Voltage: 5.9483 volts
Average Null Voltage 2: 7.8098 volts
Average Calibration Weight Voltage: −7.9146 volts
Average Gas Density: 0.1239 g/cc The weight of the calibration standard is determined, in volts, from the difference between the average null voltage 2 and the average calibration weight voltage at both ambient and high pressure. Thus, the voltages $v_{a1}$ and $v_{a2}$ in equation (14) are 15.8595 volts and 15.7244 volts, respectively, for ambient and high pressure. Thus, for this example, $C_1/C_2 = 0.997584$.

The unknown density of the sample is now determined using equation (14) and the known ratio of $C_1/C_2$. The weight of the sample is determined, in volts, from the difference between the null voltage 1 and the sample voltage at ambient and high pressure. Thus, the voltages $v_{a1}$ and $v_{a2}$ for equation (14) are 1.9516 volts and 1.8611 volts, respectively, for ambient and high pressure. Using the ratio $C_1/C_2$ determined with the tungsten calibration standard, the density of the sample is determined to be 2.689 g/cc, which compares well with the theoretical value of 2.699 g/cc.

With reference again to FIG. 3, the density of the gas 13 in the chamber 212 is preferably changed by adjusting the pressure of the gas 13 using the pressure regulator 40 while the temperature in the chamber 212 remains constant. In an alternative embodiment, the density of the gas 13 may be changed by adjusting the temperature in the chamber 212 while maintaining a constant pressure. In this alternative embodiment, the system 210 includes a temperature regulation unit 56 which is preferably controlled by the processing unit 46. The temperature regulation unit 56 includes heating and cooling elements attached to the chamber 212 which provide for varying the temperature in the chamber 212 over a wide enough range to provide a variation in gas density of about 0.015 g/cc, similar to the change in the preferred embodiment. In this alternative embodiment, it is possible to change the gas density by approximately 0.015 g/cc at 375 psi by changing the temperature by 20° C. to 50° C. Once the gas density is determined based on the temperature and pressure measurements at several temperature increments, the determination of the sample density proceeds in the same manner as that described previously.

In another alternative embodiment of the invention, the apparatus of FIG. 3 is used to determine the density of a fluid medium, such as a gas, based on the known density of an object. Recall that the apparent weight of a sample, $F_a$, as expressed by equation (5), is the true weight of the sample, mg, minus the buoyancy force, $\rho Vg$, where $\rho$ is the density of the gas:

$$F_a = mg - \rho Vg. \quad (5)$$

Based on equation (5), the density of the gas may be expressed as:

$$\rho = \frac{mg - F_a}{Vg}. \quad (17)$$

Thus, if the mass and volume of the sample are known precisely, the density of the gas at any particular temperature and pressure may be determined based on the measurement of $F_a$ using the system shown in FIG. 3. Using the temperature regulation system 56, the density of the gas may be determined at several temperatures of interest.

Although the preferred embodiment as described herein measures density of one sample at a time, it is conceived that other embodiments of the invention may include means to move multiple samples into and out of the chamber 212 without opening the access door 362.

In another, embodiment, the current invention is used to measure the bulk modulus, K, or compressibility, $\beta$, of a solid. The bulk modulus describes the decrease in volume due to a hydrostatic pressure acting on the sample, such as the pressure applied in the device described in FIGS. 2 or 3, and is given by:

$$K = \frac{\sigma}{\Delta V / V_1}, \quad (18)$$

where $\sigma$ is the pressure of the gas 13, $\Delta V$ is the change in volume of the sample due to the applied pressure, and $V_1$ is the original volume at the initial pressure. Such a method would be convenient for evaluating the elastic properties of low modulus materials, such as polymers and closed-pore foams, which cannot be evaluated by conventional tensile methods or indentation methods.

To aid in understanding how bulk modulus, or compressibility, is measured using the present invention, the general concept of the relationship between hydrostatic strains and buoyancy forces is first reviewed. Referring to equation (18), the bulk modulus, K, is a constant of proportionality between hydrostatic stress (applied in the preferred embodiment of this invention by gas pressure) and the volumetric strain. This invention relates to a method for rendering the volumetric strain from weight measurements using the apparatus described above, where the measured quantities are gas pressure, gas temperature, and the apparent weight of the sample.

Referring to FIG. 13, a cube, C, of a compressible material is depicted inside a chamber held at a fluid pressure, P. If the same compressible cube is subjected to different fluid pressures ($P_1$, $P_2$, $P_3$) the sample will assume different volumes. More specifically, as the pressure increases ($P_3 > P_2 > P_1$), the sample becomes more compressed and occupies a smaller volume. The implication is that the buoyancy force (right hand term in equation (5)) is no longer a linear function of gas density, $\rho$, i.e., the volume is also a function of gas pressure.

Figure 14:
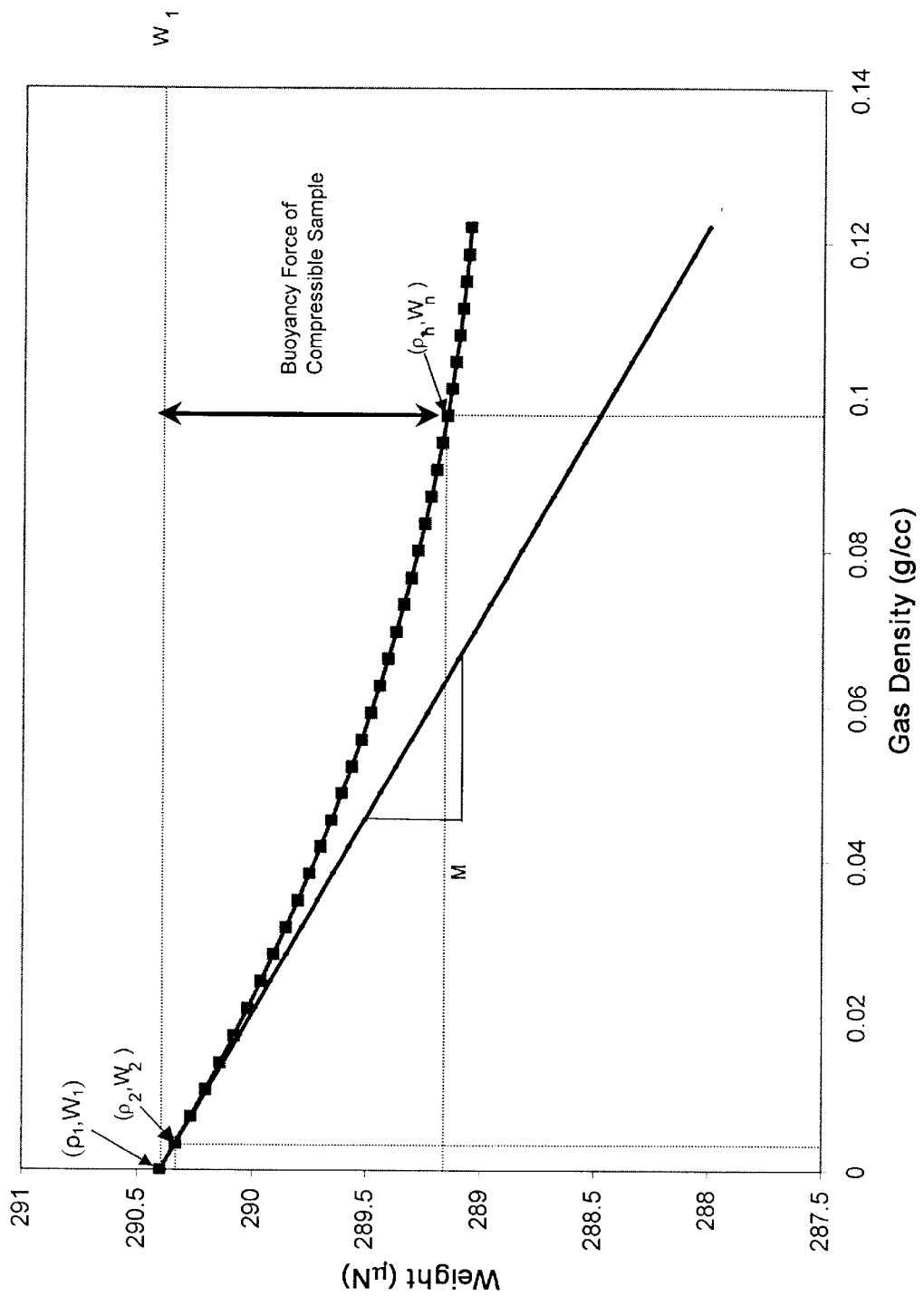
FIG. 14 graphically depicts a relationship between gas density and apparent weight of a sample of compressible material.

To determine volumetric strain, the initial volume $V_1$ and the change in volume $\Delta V$ need to be rendered from the schematic curve in FIG. 14. To determine the bulk modulus, or compressibility, volumetric strain is preferably measured as a function of gas pressure. For illustrative purposes, consider a hypothetical sample of compressible matter with weight of approximately 290.4 $\mu$N in vacuum. The weight of the sample is measured as continuously as possible as the chamber is slowly pressurized to increase the gas density (see FIG. 14). This is preferably achieved by making weight measurements as the gas pressure is changed in small increments.

In the preferred embodiment of the invention, the volumetric strain in the sample is calculated at each increment in gas density (or gas pressure) in FIG. 14. At each gas density increment ($\Delta \rho = 0.98$ g/cc, for example) the volumetric strain is preferably calculated according to $$\frac{\Delta V}{V_1} = \frac{V_n - V_1}{V_1}, \quad (19)$$

where $V_1$ is the initial volume of the compressible sample at the initial gas pressure, and $V_n$ is the sample volume at an nth gas pressure, or gas density.

Generally, equation (5) is valid for any sample, whether the sample is compressible or incompressible. That is, the apparent weight of the sample is always the weight in vacuum, mg, minus the buoyancy force, which is the weight of the displaced fluid. Equation (5) is used in this embodiment of the invention to determine both the initial volume and any subsequent volume along the curve in FIG. 14.

First, preferred methods of determining initial volume are described. At the initial gas density in FIG. 14, the slope M of the curve is exactly the same for the compressible sample as it would be for an incompressible sample of precisely the same initial volume. Therefore, based on equation (5), the initial slope of the curve in FIG. 14 is given by $$M = -V_1 \times g, \text{ or} \tag{20a}$$

$$V_1 = -\frac{M}{g}, \quad \text{where} \tag{20b}$$

$$M = \frac{\rho_2 - \rho_1}{W_2 - W_1}. \tag{20c}$$

Substituting equation (20c) into equation (20b), the initial volume of the sample may be expressed as:

$$V_1 = -\frac{\rho_2 - \rho_1}{g(W_2 - W_1)}. \tag{20d}$$

In alternative preferred embodiments, the slope M or initial volume $V_1$ may be determined by measuring many data points of apparent weight and fluid density, and fitting a curve to the data points.

Second, at all additional points along the curve in FIG. 14, equation (5) is used to determine the instantaneous volume, $V_n$, as follows. Rearranging equation (5), the volume $V_n$ is given by $$V_n = \frac{W_1 - W_n}{(\rho_n - \rho_1)g} \tag{21}$$

where $W_1$ is the initial weight at the initial gas density $\rho_1$, and $W_n$ is the apparent weight at some other gas density, $\rho_n$. Based on measured quantities, equation (20) is solved for $V_1$ and inserted into equation (19) along with $V_n$ from equation (21) to yield an expression for volumetric strain:

$$\frac{\Delta V}{V_1} = \frac{V_n}{V_1} - 1 = \frac{(W_1 - W_n)}{M(\rho_1 - \rho_n)} - 1. \tag{22}$$

Equation (22) is preferably evaluated at N number of data points ($\rho_n$, $W_n$, for n=1 to N) along the curve in FIG. 14 to obtain volumetric strain as a function of gas density.

In the preferred embodiment for measuring bulk modulus, an equation of state is used to relate the measured gas temperature and pressure to the gas density. Thus, for each gas density used in equation (22), there is a known corresponding gas pressure. This known relationship between gas pressure and gas density is preferably used to construct the stress-strain curve. In the preferred embodiment, the stress-strain curve is constructed by plotting the volumetric strains in equation (22) as a function of gas pressure. The slope of the resulting stress-strain curve is the proportionality constant, K, from equation (18).

Figure 15A:
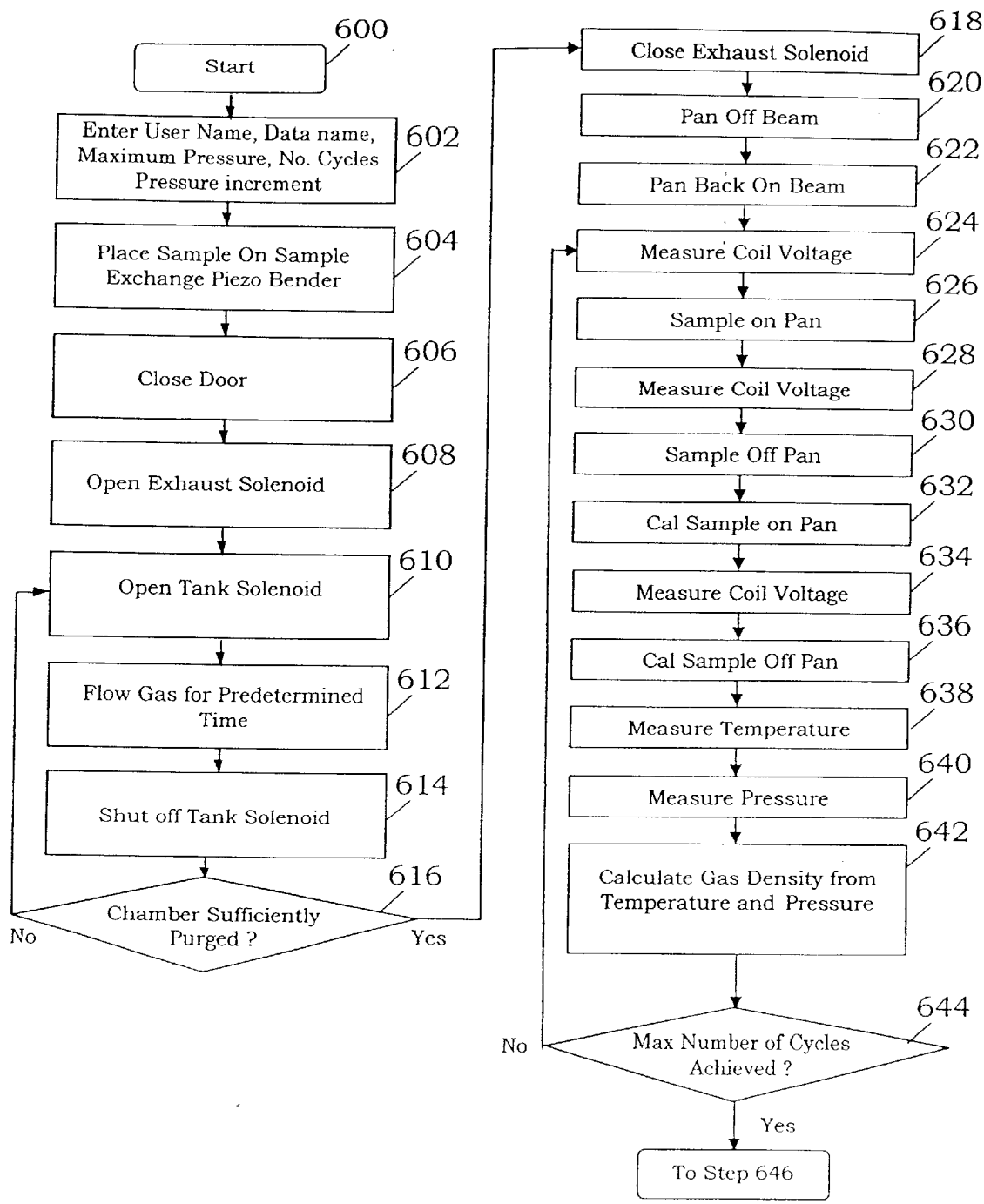
FIGS. 15A–15B depict a functional flow diagram for a method for determining bulk density of a sample according to a preferred embodiment of the invention.
Figure 15B:
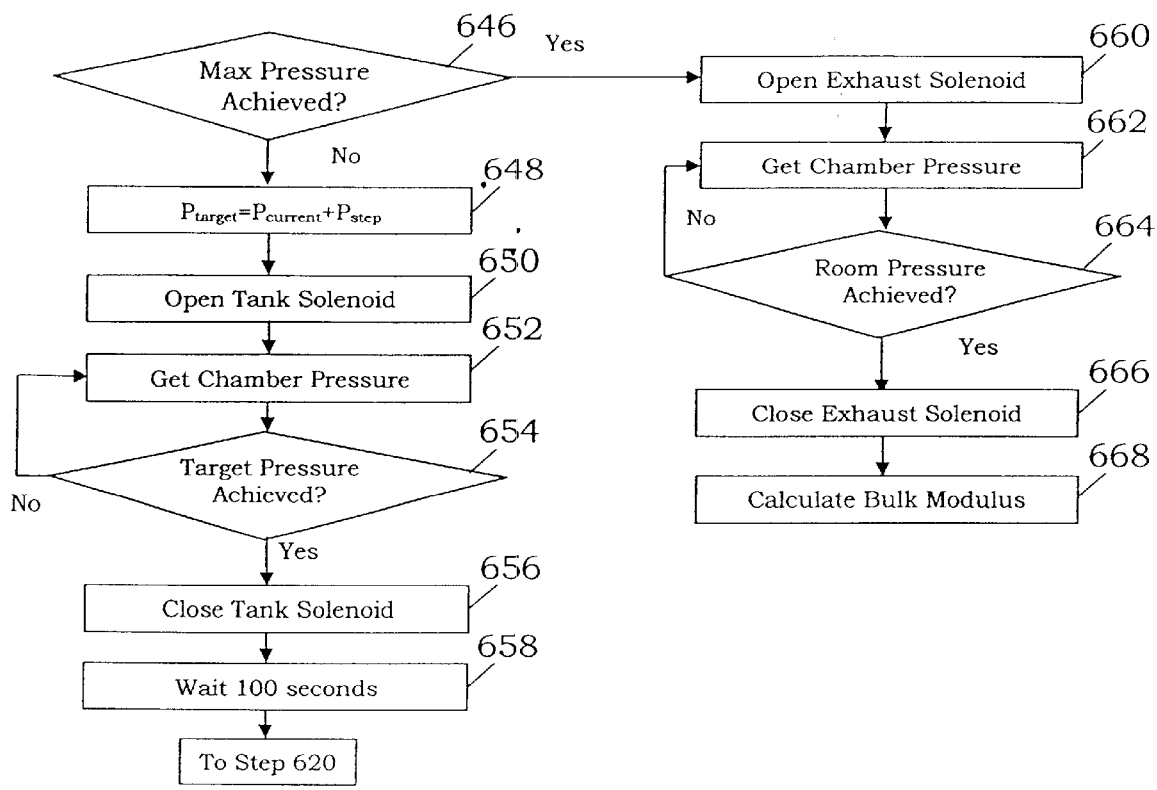

Referring to FIGS. 15A–15B, the step-by-step operation of the apparatus 210 for measuring bulk modulus, or compressibility, according to the preferred embodiment of the invention is next described. In the preferred embodiment, the apparatus 210 (FIG. 3) is controlled by the computer 35, and data is logged by the processing unit 46 using software instructions contained within one or more software programs.

To begin a test, a test operator begins execution of the software program (step 600) and follows prompts and requests provided by the program via the monitor 54. Preferably, the operator enters, via the keyboard 52, the operator's name, a unique identifier for the test, the maximum gas pressure, the number of purge cycles, a pressure increment, and the number of measurement cycles (step 602). The unique identifier for the test is preferably stored with the data so that the data can be easily retrieved at later time.

With reference to FIGS. 4A–4B and 11A–11C, a sample 355 is placed manually on the sample holder 376 of the chamber door assembly 362 (step 604), and the removable door 364 of the chamber 212 is replaced and secured (step 606). Details of operating the door have already been discussed in regards to step 404 in FIG. 10A.

The program preferably pauses through the sample introduction step 604 and waits until the door is closed (step 606). The program resumes when the user clicks an "OK" button in the software, indicating that the sample has been introduced and the door assembly 362 is closed. From this point forward the operation of the preferred embodiment of the invention is completely operated by the computer 35.

The chamber vent valve 215 (FIG. 3) is opened (step 608), and a second solenoid valve 250 is opened to allow the gas 13 to run into the chamber 212 from the high-pressure tank 42 via the mechanical pressure regulator 40 (step 610). The gas is allowed to flow for a predetermined time, thereby flushing the chamber 212 of unwanted air and replacing it with $C_2F_6$. At the end of the predetermined time, the tank solenoid 250 is closed (step 614) and is followed by a 15 second wait. This process, as indicated at steps 610–616 of FIG. 15A, is repeated a predetermined number of times (entered at step 602). Note that the number of purge cycles may be variable; thus, the purging process could be accomplished at other pressures, other numbers of cycles, or longer or shorter wait periods.

The exhaust solenoid 215 is closed (step 618) and the system begins to make weight measurements at ambient pressure in the $C_2F_6$ according to the following preferred procedure. Preferably, the weighing device 275 has a mechanism for realigning the pan assembly 320 on the knife edge 325 that is affixed to the beam 295. That mechanism, which is preferably a piezoelectric bender 256, as shown in FIGS. 4A–4B, physically picks up the pan assembly 320 by two outer tabs 328 on the pan 321 (step 620). Preferably, the bender 256 is actuated such that it bends through its maximum deflection of 2 mm over approximately 10 seconds. After a program pause of roughly 15 seconds, the pan is replaced on the beam by bending the piezoelectric bender 256 in the opposite direction (step 622). After a wait of approximately 30 seconds, the current provided to the coil 302 is measured by the data acquisition unit 48. As previously described, the coil current is determined by measuring the voltage drop across a precise load resistor in the PID loop of the closed-loop-controller 30 (step 624). This coil current represents a "zero" or "null" for the balance.

Once a steady measurement of the coil current has been obtained, the sample 355 is placed on the sample pedestal 324 of the pan assembly 320 (step 626). When the door assembly 362 was secured to the rest of the chamber 212 (step 606), the sample holder 376 holding the sample 355 was positioned directly above the sample pedestal 324. Thus, when the sample piezoelectric bender 372 is actuated by the program control, the sample weight is applied to the pan assembly 320. The closed-loop-controller 30 actively finds the required coil current required to keep the beam 295 balanced with the added sample weight 355 on the pan assembly 320. This coil current is measured (step 628) and is a representation of the sample weight. After the coil current measurement is completed, the sample piezoelectric bender 372 is activated in the opposite direction, thereby removing the sample 355 from the sample pedestal 324 of the pan assembly 320 (step 630).

The calibration sample is then placed on the pan cross piece 323 (FIG. 7A–7B) by activating a third piezoelectric bender 257 (step 632). The calibration sample is preferably a high-purity tungsten foil (0.004 inches thick) which is cut in the shape of a circle with a diameter of about 0.28 inches. The calibration sample normally resides within the chamber 212 and is inaccessible by the user. Preferably, the coil current is measured by the voltage drop across the load resistor in the closed-loop-controller 30 and is a representation of the calibration standard weight (step 634). The calibration standard is then removed from the pan cross piece 323 by activating the piezoelectric bender 257 in the opposite direction (step 636).

As discussed above, there are preferably three measurements made by the system during a test: the weight, the gas temperature, and the gas pressure. Just described in steps 624 through 636 was the method of weighing the pan, the sample, and the calibration standard. Next the program running in the processing unit 46 preferably determines the gas temperature (step 638), preferably by making about 20,000 voltage measurements across the resistance bridge in the temperature signal conditioner 238 at a rate of about 100,000 samples per second. The voltage measurement is converted immediately to a temperature through a temperature calibration, as previously discussed. Finally, the gas pressure is acquired (step 640) through a serial port by requesting a pressure from the pressure transducer 232. All five measurements are preferably transferred to the hard drive 50, or to a memory device, connected to the computer 35.

At step 642, the program calculates gas density from gas pressure and temperature measurements (steps 638 and 640). The preferred methods for calculating gas density were discusses previously with respect to step 442 in FIG. 10A. The calculated gas density is preferably stored on the hard drive 50 with the other acquired data.

The steps of measuring the pan weight, sample weight, calibration standard weight, and gas density are preferably repeated (step 644) a number of times as predetermined in step 602. Although in the preferred embodiment of the invention the weight measurements are made in a particular order, i.e., pan, sample, calibration weight, one skilled in the art will appreciate that this particular order is not critical to operation of the invention.

Once the predetermined number of data sets are acquired, the program preferably answers the question (step 646) whether the current gas pressure is greater than the maximum pressure specified in step 602. If the maximum pressure has not been reached, a new target pressure is preferably calculated by adding a pressure increment (provided at step 602) to the current pressure measured in step 640. This pressure increment is typically about 4 psi, although the exact value is not critical to the operation of the invention. At step 650 the computer opens the solenoid valve 250 and pressurizes the chamber 212 to a predetermined value from step 602 (steps 650 through 656). As the pressure in the chamber 212 increases, the program continues to monitor the internal pressure of the chamber 212 by querying the pressure transducer 232 (step 652). After each pressure measurement (step 652), the query is made whether the target pressure has been reached (step 654). If the system has not achieved the target pressure, it returns to make a new pressure measurement. If the measured pressure is greater than the target pressure, the tank solenoid 250 is closed (step 656). The program then pauses for a predetermined time, such as 100 seconds, to allow the gas and parts of the weighting device to thermally stabilize (step 658). The program execution then preferably returns to step 620 to weigh the pan, sample, and calibration weight at the new gas pressure.

In the preferred embodiment of the invention, the process of gradually increasing the gas pressure and making weight measurements (steps 620 through 658) continues until the chamber gas pressure exceeds the maximum pressure (step 646) established at step 602.

The program opens the exhaust solenoid valve 215 and depressurizes the chamber 212 to room pressure (steps 660 through 664). As the pressure in the chamber 212 decreases, the program continues to monitor the chamber pressure via the pressure transducer 232 and compares it with the ambient pressure (steps 660 through 664). When the desired pressure is attained, the program preferably closes the exhaust solenoid valve 215 (step 666).

At this point in the preferred embodiment of the invention for measuring the bulk modulus, or compressibility, program execution proceeds to calculating the bulk modulus of the sample based on the measurements described in FIGS. 15A and 15B.

For the same reasons described previously with regards to measuring density, the force calibration of the beam balance (relation between weight and coil voltage) changes with time and/or gas pressure around the beam balance. The same characteristic influences the weight measurements when measuring the bulk modulus of matter using the apparatus. As mentioned previously, the calibration standard is preferably a 99.95% pure tungsten foil 0.004 inches thick and 0.28 inches in diameter. The foil of the preferred embodiment was provided by Alfa Aesar of Ward Hill, Mass. Although the size is arbitrary, it is desirable that it is a large fraction of the load range of the apparatus. The material is also arbitrary, although it must be of known density, since it is being used as a calibration material.

Following is an example which demonstrates how the stress-strain curve and bulk modulus of a compressible closed-cell foam can be determined using the invention. First, using the same procedures described above, equation (13) is used to measure the change in load calibration. In the preferred embodiment of the invention, the ratio $C_1/C_n$ is measured at every pressure step during the bulk modulus experiment. That is, at every $n^{th}$ pressure step, the calibration weight (difference between the coil voltage with and without the calibration weight on the pan) and gas density are measured. Specifically, Equations (13) and (14) are used to determine $C_1/C_n$ based on the apparent weight of the calibration sample at the initial gas density and the apparent weight of the calibration sample at each subsequent pressure step.

Figure 16:
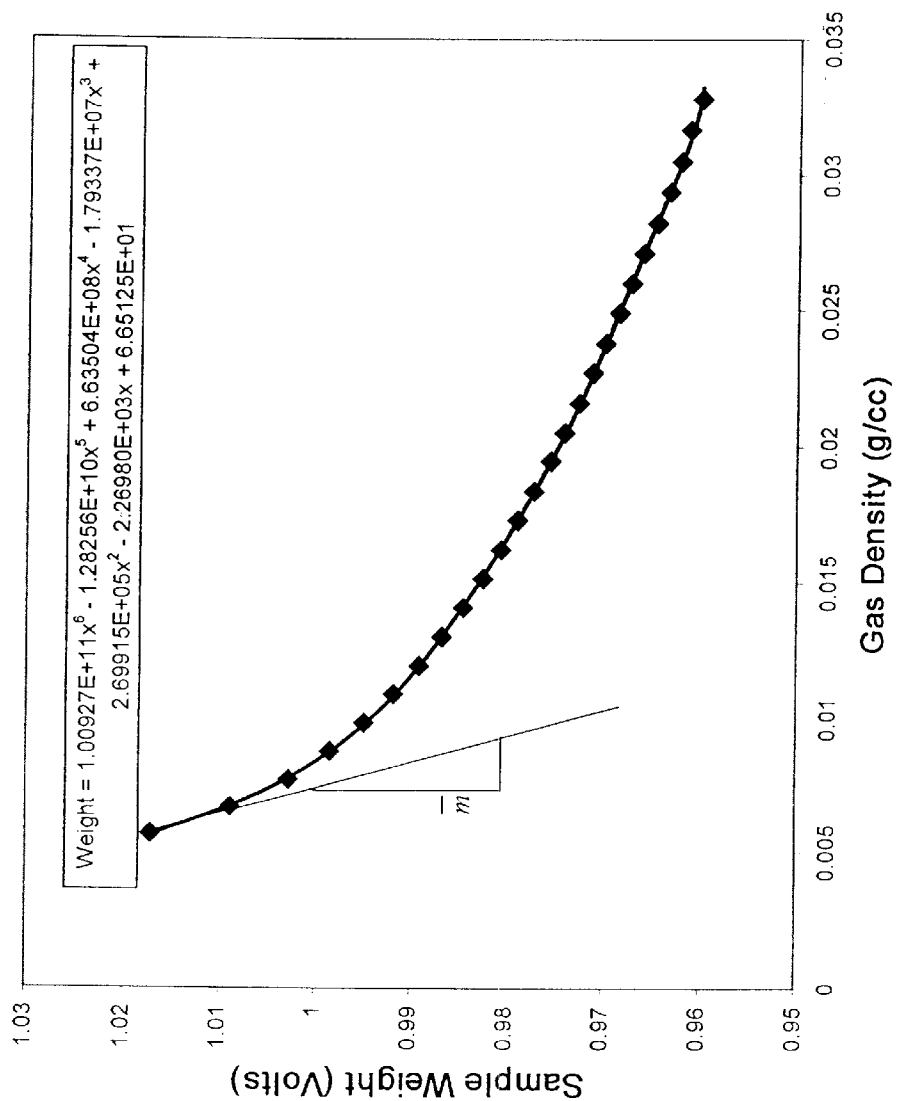
FIG. 16 graphically depicts a relationship between gas density and apparent weight of a sample of a particular compressible material.

Next, all of the measured coil voltages for the sample (except at room pressure) are multiplied by $C_n/C_1$, and equation (22) is preferably used to determine the volumetric strain. Note that it is not required that the instrument measure weight explicitly as shown in equation (22). Equation (22) may be expressed in terms of measured voltages, gas densities, and the ratio $C_n/C_1$ as:

$$\frac{\Delta V}{V_1} = \frac{(W_1 - W_n)}{M(\rho_1 - \rho_n)} - 1 = \frac{(C_1 v_1 - C_n v_n)}{C_1 M(\rho_1 - \rho_n)} - 1 = \frac{\left(v_1 - \frac{C_n}{C_1} v_n\right)}{M(\rho_1 - \rho_n)} - 1, \quad (23)$$

where $v_1$ is the initial coil voltage at the initial gas density $\rho_1$, $v_n$ is any subsequent coil voltage at a subsequent gas density $\rho_n$, M is the initial slope of the weight versus gas density curve in volts/(g/cc), and $C_n/C_1$ is the ratio defining how much the load-calibration has changed relative to the initial measurement at the initial gas density $\rho_1$. For illustrative purposes, the corrected sample weight ($C_n/C_1 \times v_n$) is plotted as a function of gas density in FIG. 16. The initial slope, M, is preferably obtained by performing a curve fit to the data in FIG. 16, differentiating with respect to gas density, and evaluating at the initial gas density, $\rho_1$.

Figure 17:
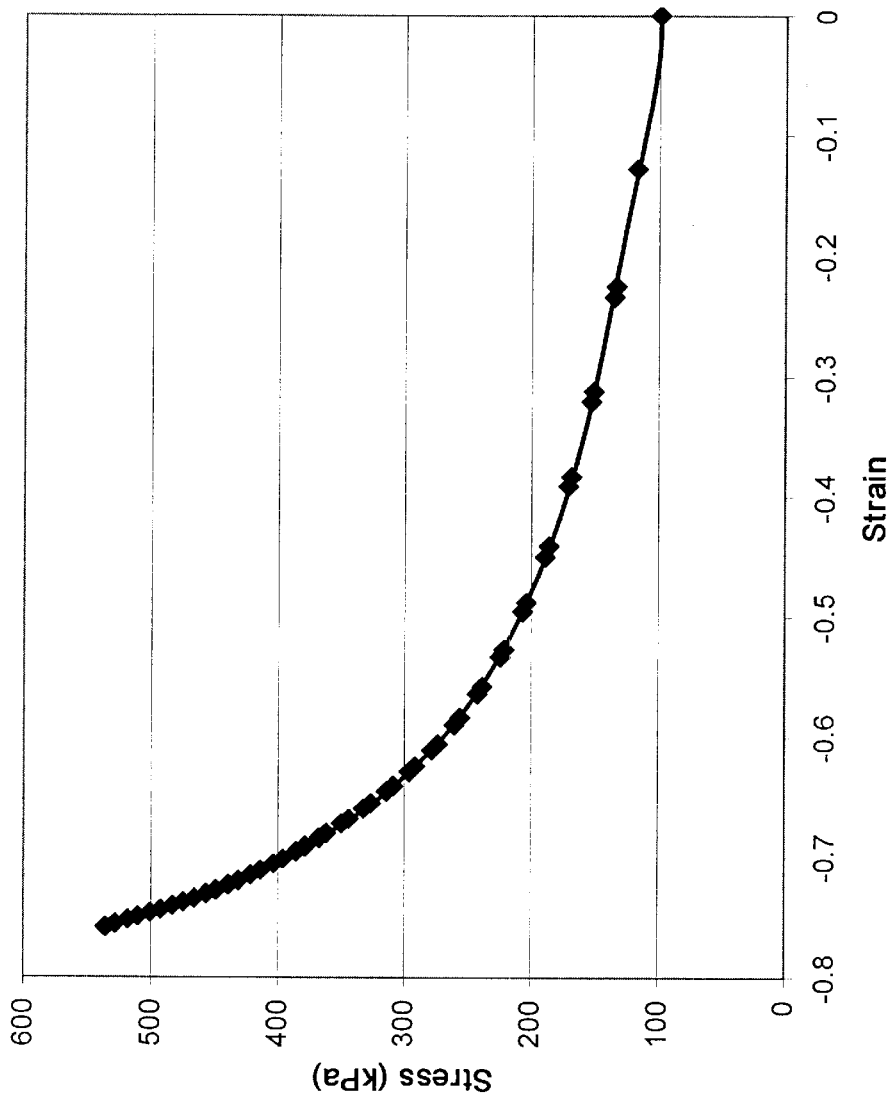
FIG. 17 graphically depicts a relationship between stress and strain in a sample of a particular compressible material.

After equation (23) has provided the volumetric strain at each pressure increment, the stress-strain curve is preferably compiled as shown in FIG. 17. For the foam used in this sample data, the slope of the stress-strain curve is not constant, and increases as the stress is increased, which is a characteristic of closed-cell foams. As the cells collapse due to the applied hydrostatic stress, the stiffness of the material increases. This is a familiar characteristic of sponge-like materials that is experienced when a sponge is squeezed. Initially the sponge is easy to compress, but as the pores collapse, the material becomes stiffer.

In yet another embodiment of the invention, instead of adjusting the pressure or temperature of the gas in the chamber 212 to adjust its density, the density of the gas may be varied by introducing a second gas into the same chamber 212, where the second gas has a significantly higher or lower density than the first gas. For example, the chamber 212 is first filled with helium gas and the apparent weight of the sample is determined. A second gas, such as $C_2F_6$, is then introduced into the chamber and is mixed with the first gas, and the apparent weight of the sample is again determined. The measured apparent weights and the difference in density between the helium gas alone and the mixture of the helium gas and the $C_2F_6$ are then used to determine the density of the sample in a manner similar to that described previously.

Alternatively, instead of mixing the first and second gases, the second gas may completely replace the first gas. For example, the chamber 212 is first filled with helium gas and the apparent weight of the sample in the helium is determined. The helium is then purged from the chamber 212, and the second gas, such as $C_2F_6$, is introduced into the chamber. The apparent weight of the sample in the $C_2F_6$ is then determined. The measured apparent weights and the difference in density between the helium gas and the $C_2F_6$ are then used to determine the density of the sample in a manner similar to that described previously.

One skilled in the art will appreciate that the method and apparatus described herein could be used with one type of gas to cover one range of gas density variation, and with another type of gas to cover another range of gas density variation to make measurements on the same sample. In this manner, the possible range of gas density variation may be extended farther than may be possible using a single gas.

Although one or more theories of operation of preferred embodiments of the invention have been presented herein, it should be appreciated that the invention is not limited by any particular theory of operation. Thus, the scope of the invention be determined based on the claims, not upon theories of operation described herein.

It is contemplated, and will be apparent to those skilled in the art from the preceding description and the accompanying drawings that modifications and/or changes may be made in the embodiments of the invention. Accordingly, it is expressly intended that the foregoing description and the accompanying drawings are illustrative of preferred embodiments only, not limiting thereto, and that the true spirit and scope of the present invention be determined by reference to the appended claims.

What is claimed is:

1. A method for determining a relationship between hydrostatic stress and volumetric strain in a sample of compressible material, where the sample is immersed in a fluid medium having a density, comprising:
    (a) varying the hydrostatic stress on the sample by changing the density of the fluid medium over a range of densities;
    (b) determining a change in apparent weight of the sample as the density of the fluid medium is changed; and
    (c) determining the volumetric strain in the sample based on the change in apparent weight of the sample and the change in density of the fluid medium.

2. The method of claim 1 wherein the fluid medium exists at a pressure related to the density, and wherein step (a) comprises changing the density of the fluid medium over a range of densities by changing the pressure of the fluid medium over a range of pressures.

3. The method of claim 1 wherein:
    step (a) further comprises changing the density of the fluid medium from a first density, $\rho_1$, to an nth density, $\rho_n$;
    step (b) further comprises determining a first apparent weight of the sample, $W_1$, at the first density and an nth apparent weight of the sample, $W_n$, at the nth density;
    step (c) further comprises determining the volumetric strain in the sample according to:

$$\frac{\Delta V}{V_1} = \frac{W_1 - W_n}{V_1 \times (\rho_1 - \rho_n)} - 1,$$

where $V_1$ is an initial volume of the sample at the first density, and $\Delta V/V_1$ is the volumetric strain.

4. The method of claim 3 wherein the initial volume of the sample $V_1$ is expressed as $$V_1 = -\frac{\rho_2 - \rho_1}{g(W_2 - W_1)},$$

where $\rho_2$ is a second density of the fluid medium which is different from the first density, $W_2$ is a second apparent weight of the sample with the fluid medium at the second density, and g is acceleration due to gravity.

5. The method of claim 1 wherein:
    step (a) further comprises:
        (a1) causing the fluid medium to have a first density, $\rho_1$;
        (a2) causing the fluid medium to have an nth density, $\rho_n$;
    step (b) further comprises:
        (b1) exposing the sample to an acceleration in a first direction while immersed in the fluid medium having the first density;
        (b2) determining a first applied force in a second direction opposite the first direction, where the first applied force is sufficient to maintain the sample in static equilibrium while the acceleration is applied and the object is immersed in the fluid medium having the first density;

(b3) exposing the sample to the acceleration in the first direction while immersed in the fluid medium having the nth density; and (b4) determining an nth applied force in the second direction which is sufficient to maintain the sample in static equilibrium while exposed to the acceleration and immersed in the fluid medium having the nth density; and step (c) further comprises determining the volumetric strain in the sample according to:

$$\frac{\Delta V}{V_1} = \frac{W_1 - W_n}{V_1 \times (\rho_1 - \rho_n)} - 1,$$

where $V_1$ is an initial volume of the sample at the first density, $$\frac{\Delta V}{V_1}$$

is the volumetric strain, $W_1$ is the first applied force, and $W_n$ is the nth applied force.

6. The method of claim 5 wherein:

step (b) further comprises:

(b5) completely immersing a calibration standard of known density in the fluid medium having the first density;

(b6) exposing the calibration standard to the acceleration in the first direction while immersed in the fluid medium having the first density;

(b7) determining a first calibration force in the second direction, where the first calibration force is sufficient to maintain the calibration standard in static equilibrium while the acceleration is applied and the calibration standard is immersed in the fluid medium having the first density;

(b8) completely immersing the calibration standard in the fluid medium having the nth density;

(b9) exposing the calibration standard to the acceleration in the first direction while immersed in the fluid medium having the nth density;

(b10) determining an nth calibration force in the second direction which is sufficient to maintain the calibration standard in static equilibrium while exposed to the acceleration and immersed in the fluid medium having the nth density; and (b11) calculating a calibration ratio based on the first and nth calibration forces, the first and nth densities of the gaseous medium, and the known density of the calibration standard; and step (c) further comprises determining the volumetric strain in the sample based on at least the first and nth densities of the gaseous medium, the first and nth applied forces, and the calibration ratio.

7. The method of claim 6 wherein step (b11) further comprises calculating the calibration ratio according to:

$$\frac{C_1}{C_n} = \frac{v_{cn}(\rho_c - \rho_1)}{v_{c1}(\rho_c - \rho_n)},$$

where $$\frac{C_1}{C_n}$$

is the calibration ratio, $\rho_C$ is the known density of the calibration standard, $v_{c1}$ is a voltage related to the first calibration force, and $v_{cn}$ is a voltage related to the nth calibration force.

8. The method of claim 7 wherein step (c) further comprises determining the volumetric strain in the sample according to:

$$\frac{\Delta V}{V_1} = \frac{\left(v_1 - \frac{C_n}{C_1}v_n\right)}{M(\rho_1 - \rho_n)} - 1,$$

where $V_1$ is a voltage related to the first applied force, $v_n$ is a voltage related to the nth applied force, and M is given by $$M = -V_1 \times g,$$

where g is the acceleration in the first direction.

9. The system of claim 1 further comprising:

step (a) including:
(a1) causing the fluid medium to have a first density by pressurizing the fluid medium to a first pressure; and
(a2) causing the gaseous medium to have an nth density by pressurizing the fluid medium to an nth pressure that is different from the first pressure;

(d) determining a first temperature of the fluid medium while the fluid medium is pressurized to the first pressure;

(e) determining an nth temperature of the fluid medium while the fluid medium is pressurized to the nth pressure;

(f) determining the first density of the fluid medium based on the first pressure and the first temperature; and (g) determining the nth density of the fluid medium based on the nth pressure and the nth temperature.

10. A method for determining volumetric strain in a sample of compressible material immersed in a fluid medium as the sample is exposed to varying hydrostatic stress, comprising:

(a) causing the fluid medium to have a first density, $\rho_1$;

(b) causing the fluid medium to have an nth density, $\rho_n$;

(c) exposing the sample to an acceleration in a first direction while immersed in the fluid medium having the first density;

(d) determining a first voltage related to a first applied force in a second direction opposite the first direction, where the first applied force is sufficient to maintain the sample in static equilibrium while the acceleration is applied and the object is immersed in the fluid medium having the first density;

(e) exposing the sample to the acceleration in the first direction while immersed in the fluid medium having the nth density;

(f) determining an nth voltage related to an nth applied force in the second direction which is sufficient to maintain the sample in static equilibrium while exposed to the acceleration and immersed in the fluid medium having the nth density;

(g) completely immersing a calibration standard of known density in the fluid medium having the first density;

(h) exposing the calibration standard to the acceleration in the first direction while immersed in the fluid medium having the first density;

(i) determining a first calibration voltage related to a first calibration force in the second direction, where the first calibration force is sufficient to maintain the calibration standard in static equilibrium while the acceleration is applied and the calibration standard is immersed in the fluid medium having the first density;

(j) completely immersing the calibration standard in the fluid medium having the nth density;

(k) exposing the calibration standard to the acceleration in the first direction while immersed in the fluid medium having the nth density; and (l) determining an nth calibration voltage related to an nth calibration force in the second direction which is sufficient to maintain the calibration standard in static equilibrium while exposed to the acceleration and immersed in the fluid medium having the nth density;

(m) calculating a calibration ratio according to:

$$\frac{C_1}{C_n} = \frac{v_{cn}(\rho_c - \rho_1)}{v_{c1}(\rho_c - \rho_n)},$$

where $$\frac{C_1}{C_n}$$

is the calibration ratio, $\rho_c$ is the known density of the calibration standard, $v_{c1}$ is the first calibration voltage related to the first calibration force, and $v_{cn}$ is the nth calibration voltage related to the nth calibration force; and (n) determining the volumetric strain in the sample according to:

$$\frac{\Delta V}{V_1} = \frac{\left(v_1 - \frac{C_n}{C_1}v_n\right)}{M(\rho_1 - \rho_n)} - 1,$$

where $$\frac{\Delta V}{V_1}$$

is the volumetric strain, $v_1$ is the voltage related to the first applied force, $v_n$ is the voltage related to the nth applied force, and M is given by $$M = -V_1 \times g,$$

where $V_1$ is the initial volume of the sample and g is the acceleration in the first direction.

11. The method of claim 10 where the slope M is expressed as $$M = \frac{\rho_2 - \rho_1}{W_2 - W_1},$$

where $\rho_2$ is a second density of the fluid medium which is different from the first density, an $W_2$ is a second apparent weight of the sample with the fluid medium at the second density.

12. A method for operating an apparatus to determine bulk modulus of a sample, the apparatus including a beam balance enclosed within a pressure chamber, the beam balance including a sample pan coupled to a first end of the beam balance and a counter-force application device disposed at an opposing second end of the beam balance, the apparatus further including a calibration standard of known density, a temperature sensor, and a pressure sensor, the method comprising:

(a) sealing the sample within the pressure chamber;

(b) purging the pressure chamber of air;

(c) pressurizing the chamber to a first pressure using a fluid medium;

(d) determining a first force applied by the counter-force application device required to balance the beam balance with the sample on the sample pan with the pressure chamber pressurized to the first pressure;

(e) measuring a first temperature within the pressure chamber using the temperature sensor with the pressure chamber pressurized to the first pressure;

(f) measuring the pressure within the pressure chamber using the pressure sensor with the pressure chamber pressurized to the first pressure;

(g) calculating a first density of the fluid medium based upon a predetermined relationship between density, pressure, and temperature of the fluid medium;

(h) pressurizing the chamber to an nth pressure, which is different from the first pressure;

(i) determining an nth force applied by the counter-force application device required to balance the beam balance with the sample on the sample pan with the pressure chamber pressurized to the nth pressure;

(j) measuring an nth temperature within the pressure chamber using the temperature sensor with the pressure chamber pressurized to the nth pressure;

(k) measuring the pressure within the pressure chamber using the pressure sensor with the pressure chamber pressurized to the nth pressure;

(l) calculating an nth density of the fluid medium based upon the predetermined relationship between density, pressure, and temperature of the fluid medium; and (m) calculating the bulk modulus of the sample based at least in part on the first and nth densities of the fluid medium and the first and nth forces applied by the counter-force application device.

13. The method of claim 12 further comprising:

(n) determining a first null force applied by the counter-force application device required to balance the beam balance with no sample or calibration standard on the sample pan with the pressure chamber pressurized to the first pressure; and (o) determining an nth null force applied by the counter-force application device required to balance the beam balance with no sample or calibration standard on the sample pan with the pressure chamber pressurized to the nth pressure.

14. The method of claim 12 further comprising:

(n) determining a first calibration force applied by the counter-force application device required to balance the beam balance with the calibration standard on the sample pan with the pressure chamber pressurized to the first pressure; and (o) determining an nth calibration force applied by the counter-force application device required to balance the beam balance with the calibration standard on the sample pan with the pressure chamber pressurized to the nth pressure.

15. The method of claim 14 wherein step (m) further comprises calculating the bulk modulus of the sample based on the first and nth densities of the fluid medium, the known density of the calibration standard, the first and nth applied forces, and the first and nth calibration forces.

16. The method of claim 14 wherein step (m) further comprises calculating a calibration ratio according to:

$$\frac{C_1}{C_n} = \frac{v_{cn}(\rho_C - \rho_1)}{v_{c1}(\rho_C - \rho_n)},$$

where $$\frac{C_1}{C_n}$$

is the calibration ratio, $\rho_c$ is the known density of the calibration standard, $\rho_1$ is the first density of the fluid medium, $\rho_n$ is the nth density of the fluid medium, $v_{c1}$ is a first calibration voltage related to the first calibration force, and $V_{cn}$ is an nth calibration voltage related to the nth calibration force.

17. The method of claim 16 wherein step (m) further comprises determining the bulk modulus of the sample according to:

$$\frac{\Delta V}{V_1} = \frac{\left(v_1 - \frac{C_n}{C_1}v_n\right)}{M(\rho_1 - \rho_n)} - 1,$$

where $$\frac{\Delta V}{V_1}$$

is the bulk modulus, $v_1$ is a voltage related to the first applied force, $v_n$ is a voltage related to the nth applied force, and M is given by $$M = -V_1 \times g,$$

where $V_1$ is an initial volume of the sample at the first density, and g is acceleration due to gravity.

18. An apparatus for determining bulk modulus of a sample having a sample mass and a sample volume while the sample is immersed in a fluid medium having variable density, and the sample is exposed to an acceleration in a first direction and a net buoyancy force in a second direction opposite the first direction, where the net buoyancy force is a sum of buoyancy forces in the first and second directions exerted on the sample by the fluid medium, the apparatus comprising:

a chamber for containing the fluid medium and the sample immersed in the fluid medium;

means for selectively varying the density of the fluid medium in the chamber over a range of densities;

means for producing at least one electrical signal related to the density of the fluid medium in the chamber as he density of the fluid medium is varied;

a beam balance disposed within the chamber and having opposing first and second ends, the beam balance further comprising:

a sample pan disposed adjacent the first end of the beam balance, the sample pan having a sample pan volume and a sample pan mass, and creating a sample pan moment adjacent the first end of the beam balance;

a first counter-weight disposed adjacent the second end of the beam balance, the first counter-weight having a first counter-weight volume which is substantially equivalent to the sample pan volume, a first counter-weight mass which is substantially equivalent to the sample pan mass, and creating a first counter-weight moment adjacent the second end of the beam balance which is substantially equivalent to the sample pan moment;

a coil assembly disposed adjacent the second end of the beam balance, the coil assembly having a coil assembly volume and a coil assembly mass, and creating a coil assembly moment adjacent the second end of the beam balance, the coil assembly electrically coupled to a controller;

a second counter-weight disposed adjacent the first end of the beam balance, the second counter-weight having a second counter-weight volume which is substantially equivalent to the coil assembly volume, a second counter-weight mass which is substantially equivalent to the coil assembly mass, and creating a second counter-weight moment adjacent the first end of the beam balance which is substantially equivalent to the coil assembly moment;

a magnet assembly disposed adjacent to and magnetically interacting with the coil assembly;

the controller for providing a coil current to the coil assembly, thereby generating a magnetic field which interacts with the magnet assembly, the interaction between the magnetic field of the coil assembly and the magnet assembly causing a force to be applied to the second end of the beam to keep the beam balanced as the density of the fluid medium in the chamber is varied over the range of densities, where the force applied to the second end of the beam is substantially equivalent to the difference between the net buoyancy force and the product of the sample mass times the acceleration while the sample is immersed in the fluid medium as the density of the gaseous medium is varied over the range of densities; and a computing device for receiving the at least one electrical signal related to the density of the fluid medium and at least one electrical signal related to the coil current, and for calculating the bulk modulus of the sample based at least in part upon the at least one electrical signal related to the density of the gaseous medium and the at least one electrical signal related to the coil current.

19. The apparatus of claim 18 wherein the means for producing the at least one electrical signal related to the density of the fluid medium comprises:

a temperature sensor disposed within the chamber for generating a temperature signal indicative of temperature of the fluid medium as the density of the fluid medium is varied over the range of densities;

a pressure transducer in fluid communication with the chamber for generating a pressure signal indicative of pressure of the fluid medium as the density of the fluid medium is varied over the range of densities;

the computing device for receiving the temperature signal and the pressure signal, and for calculating, based upon a predetermined relationship between pressure, temperature, and density of the fluid medium, the corresponding density of the fluid medium as the density of the fluid medium is varied over the range of densities.

20. The apparatus of claim 18 further comprising:

a first actuator for placing the sample pan on and removing the sample pan from the first end of the beam balance;

a second actuator for placing the sample on and removing the sample from the sample pan; and a third actuator for placing a calibration standard on and removing the calibration standard from the sample pan.

21. The apparatus of claim 18 further comprising:

the beam balance having an aperture therein disposed adjacent the second end;

a light emitter disposed adjacent the second end of the beam balance for emitting light toward one side of the aperture in the beam balance;

a dual-detector circuit disposed adjacent the second end of the beam balance and on an opposing side of the aperture from the light emitter, the dual-detector circuit for receiving light emitted from the light emitter which passes through the aperture, and, based thereon, for generating an error signal indicative of the position of the aperture relative to the dual-detector assembly;

the controller for receiving the error signal and for generating the coil current to cause the second end of the beam balance to move to a balanced position as indicated by the error signal.

22. The apparatus of claim 18 further comprising:

the coil assembly including:
  an annular copper coil electrically coupled to the controller; and
  an annular damping ring disposed about the copper coil; and the magnet assembly disposed at least partially within the copper coil.

23. The apparatus of claim 18 further comprising:

the means for selectively varying the density of the fluid medium in the chamber over a range of densities comprising means for selectively varying the density of the fluid medium in the chamber from a first density $\rho_1$ to an nth density $\rho_n$;

the means for producing at least one electrical signal related to the density of the fluid medium in the chamber comprising means for producing at least one electrical signal related to the first density $\rho_1$ and the nth density $\rho_n$;

the controller for providing a first coil current to the coil assembly, thereby causing a first force to be applied to the second end of the beam to keep the beam balanced when the fluid medium in the chamber is at the first density, and for providing an nth coil current to the coil assembly, thereby causing an nth force to be applied to the second end of the beam to keep the beam balanced when the fluid medium in the chamber is at the nth density; and the computing device for calculating the bulk modulus of the sample according to:

$$\frac{\Delta V}{V_1} = \frac{v_1 - v_n}{V_1 \times (\rho_1 - \rho_n)} - 1,$$

where $$\frac{\Delta V}{V_1}$$

is the bulk modulus, $V_1$ is an initial volume of the sample at the first density, $v_1$ is a signal related to the first coil current, and $v_n$ is a signal related to the nth coil current.

* * * * *